United States Patent
Rao et al.

(10) Patent No.: US 9,675,713 B2
(45) Date of Patent: Jun. 13, 2017

(54) NANOPROBES FOR SENSING OF REACTIVE OXYGEN AND REACTIVE NITROGEN SPECIES

(71) Applicant: The Board of Trustees of the Leland Stanford Junior University, Palo Alto, CA (US)

(72) Inventors: Jianghong Rao, Sunnyvale, CA (US); Kanyi Pu, Mountain View, CA (US); Adam Shuhendler, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 836 days.

(21) Appl. No.: 13/928,520

(22) Filed: Jun. 27, 2013

(65) Prior Publication Data
US 2014/0004049 A1 Jan. 2, 2014

Related U.S. Application Data

(60) Provisional application No. 61/666,289, filed on Jun. 29, 2012.

(51) Int. Cl.
*A61K 49/00* (2006.01)
(52) U.S. Cl.
CPC ...... *A61K 49/0093* (2013.01); *A61K 49/0032* (2013.01); *A61K 49/0054* (2013.01)
(58) Field of Classification Search
None
See application file for complete search history.

(56) References Cited

U.S. PATENT DOCUMENTS

2004/0175696 A1* 9/2004 Ullman ............... G01N 33/542
435/6.12

OTHER PUBLICATIONS

Johansson, M.K., et al., "Choosing Reporter-Quencher Pairs for Efficient Quenching Through Formation of Intramolecular Dimers", Methods in Mol. Biol., Humana Press, 2007, pp. 17-29.*
Kandel, P.K., et al., "Incorporating functionalized polyethylene glycol lipids into reprecipitatedconjugated polymer nanoparticles for bioconjugation and targeted labeling of cells", Nanoscale, 2011, pp. 1037-1045.*
Robaszkiewicz, A., et al., "Estimation of antioxidant capacity against peroxynitrite and hypochlorite with fluorescein", 2010, Talanta, pp. 2196-2198.*
Kim, M.S., et al., "Complex Nanoparticle of Light-Emitting MEH-PPPV with Au: Enhanced Luminescence", ACS Nano, 2009, pp. 1329-1334.*
Lee, H., et al., "Fluorescent Gold Nanoprobe Sensitive to Intracellular Reactive Oxygen Species", Adv. Dunct. Mater., 2009, pp. 1884-1890.*
Duan, J., et al., "Oxidative depolymerization of polysaccharides by reactive oxygen/nitrogen species", Glycobiology, 2011, pp. 401-409.*
Ogawa, K., et al., "Polyelectrolyte-Based Fluorescent Sensors", Organic Semiconductors in Sensor Applications, 2008, pp. 39-60.*
Mehrdad, A., et al., "Kinetic study of degradation of Rhodamine B in the presence of hydrogen peroxide and some metal oxide", Chem. Eng. J., 2011; pp. 1073-1078.*
Mancini, MM et al., Oxidative Quenching and Degradation of Polymer-Encapsulated Quantum Dots: New Insights into the Long-Term Fate and Toxicity of Nanocrystals in vivo, Journal of the American Chemical Society, 2008, pp. 10836-10837, vol. 130, issue 33.
Oushiki, D et al., Development and Application of a Near-Infrared Fluorescence Probe for Oxidative Stress Based on Differential Reactivity of Linked Cyanine Dyes, Journal of the American Chemical Society, 2010, pp. 2795-2801, vol. 132, issue 8.
Panizzi, P et al., Oxazine Conjugated Nanoparticle Detects in Vivo Hypochlorous Acid and Peroxynitrite Generation, Journal of the American Chemical Society, 2009, pp. 15739-15744, vol. 131, issue 43.
Koide, Y et al., Design and Synthesis of Fluorescent Probes for Selective Detection of Highly Reactive Oxygen Species in Mitochondria of Living Cells, Journal of the American Chemical Society, 2007, pp. 10324-10325, vol. 129, issue 34.
Kundu, K et al., Hydrocyanines: A Class of Fluorescent Sensors That Can Image Reactive Oxygen Species in Cell Culture, Tissue, and In Vivo, Angewandte Chemie International Edition, 2009, pp. 299-303, vol. 48.
Chan, J et al., Reaction-based small-molecule fluorescent probes for chemoselective bioimaging. Nature Chemistry, Dec. 2012, pp. 973-984, vol. 4.
Lim, MH et al., Visualization of nitric oxide in living cells by a copper-based fluorescent probe, Nature Chemical Biology, Jul. 2006, pp. 375-380, vol. 2, issue 7.
Belousov, VV et al., Visualization of nitric oxide in living cells by a copper-based fluorescent probe. Nature Methods, Apr. 2006, pp. 281-286, vol. 3, issue 4.
Jin, H et al., Detection of single-molecule H2O2 signalling from epidermal growth factor receptor using fluorescent single-walled (Continued)

*Primary Examiner* — Michael G Hartley
*Assistant Examiner* — Lance Rider
(74) *Attorney, Agent, or Firm* — Thomas|Horstemeyer, LLP

(57) ABSTRACT

For whole animal in-situ and real-time imaging of inflammation, a dual-color fluorescent nanoprobe is provided for the detection of reactive oxygen and nitrogen species (RONS) in inflammatory microenvironments. The nanoprobes of the disclosure are a RONS-responsive energy transferring nanosystem of a fluorescent conjugated polymer core and a PEG-shell linked with RONS-sensing antennae as a FRET acceptor. These nanoprobes allow in vivo imaging of the entire process of inflammation from the release of local tissue distress signals, to the action of leukocytes and macrophages late in the process of inflammation, through to restitution, allowing in whole-body diagnosis and monitoring of inflammatory diseases.

10 Claims, 22 Drawing Sheets

(56) References Cited

OTHER PUBLICATIONS carbon nanotubes. Nature Nanotechnology, Apr. 2012, pp. 302-309, vol. 5.

* cited by examiner

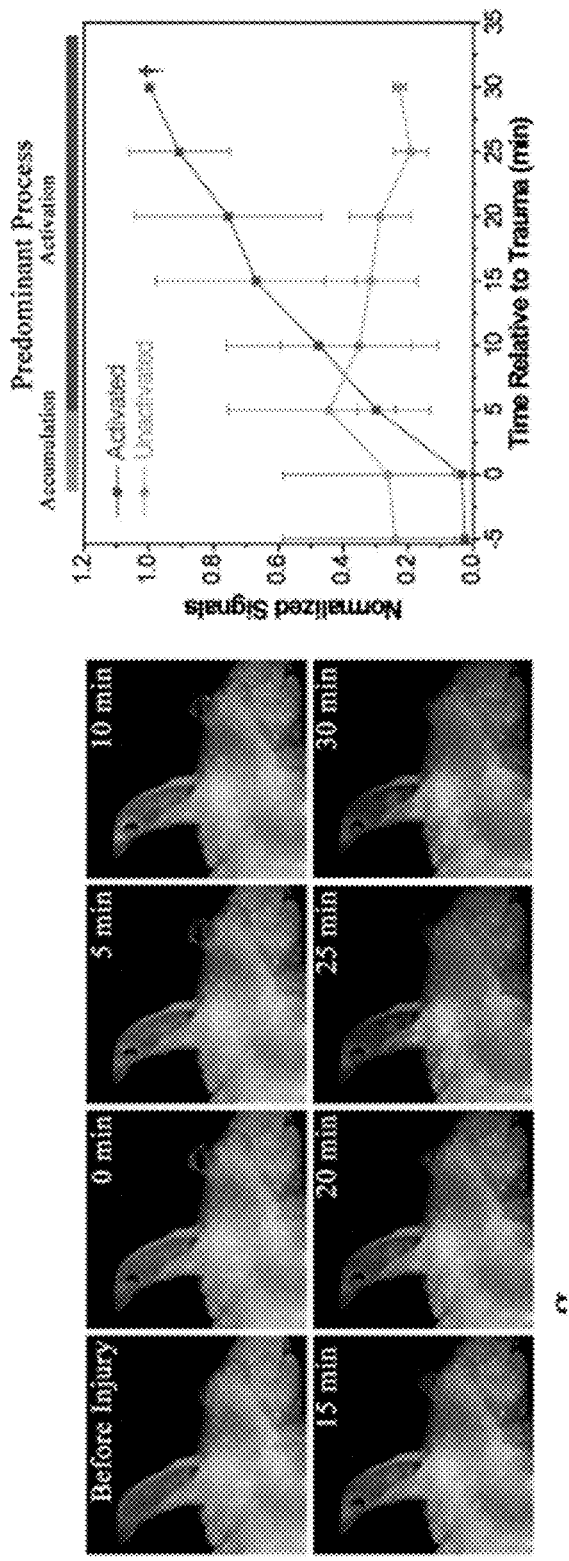
Fig. 3E
Fig. 3F
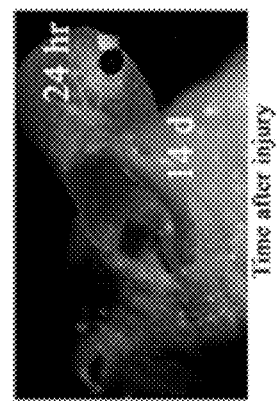
Fig. 3G

NANOPROBES FOR SENSING OF REACTIVE OXYGEN AND REACTIVE NITROGEN SPECIES

CROSS-REFERENCE TO RELATED APPLICATION

This application claims priority to U.S. Provisional Patent Application Ser. No. 61/666,289 entitled "NANOPROBES FOR SENSING OF REACTIVE OXYGEN AND REACTIVE NITROGEN SPECIES" filed on Jun. 29, 2012, which is hereby incorporated by reference in its entirety.

STATEMENT REGARDING FEDERALLY SPONSORED RESEARCH OR DEVELOPMENT

This invention was made with Government support under contracts CA135294 and CA138353 awarded by the National Institutes of Health. The Government has certain rights in the invention.

FIELD OF THE DISCLOSURE

The present disclosure relates to a self-quenching nanoparticle probe that is detectably activated by a reactive oxygen or nitrogen species at a site of inflammation in an animal or human. The present disclosure further relates to a method of identifying a site of inflammation by administering the nanoparticle probe to an animal or human.

BACKGROUND

Inflammation plays a key role in many pathophysiological processes ranging from acute inflammation associated with ischemic/reperfusion or sterile injury, to chronic inflammation in response to bacterial infection, tumor growth, cardiovascular disease, or arthritis (Carden & Granger (2000) *J. Pathol.* 190: 255-266; Kvietys & Granger (2012) *Free Radic. Biol. Med.* 52: 556-592; Libby et al., (2009) *J. Am. Coll. Cardiol.* 54: 2129-2138; Medzhitov, R. (2008) *Nature* 454: 428-435; Querfurth & LaFerla (2010) *N. Engl. J. Med.* 362: 329-344; Zeyda & Stulnig (2009) *Gerontology* 55: 379-386). The ability to determine when and where inflammation is occurring is critical to both understanding the etiology of these diseases and optimizing therapeutic interventions against these potentially life-threatening acute and chronic conditions. Reactive oxygen and nitrogen species (RONS) are integral chemical mediators of both acute and chronic inflammation (Granger & Senchenkova (eds.) (2010) Inflammation and the Microcirculation. (Morgan and Claypool Life Sciences, San Rafael, Calif.)), and their generation occurs locally and early (within minutes) in the inflammatory process, preceding the arrival of inflammatory cells (e.g. non-resident macrophages, leukocytes) (Kvietys & Granger (2012) *Free Radic. Biol. Med.* 52: 556-592). Monitoring RONS levels thus provides an opportunity for molecular imaging of inflammation, the realization of which with high in vivo spatial and temporal resolution is however challenging and has yet to be achieved.

Most existing small-molecule and genetically encoded RONS imaging probes can only function in cell culture (Albers et al., (2006) *J. Am. Chem. Soc.* 128: 9640-9641; Belousov et al., (2006) *Nat. Methods.* 3: 281-286; Koide et al., (2007) *J. Am. Chem. Soc.* 129: 10324-10325; Lim et al., (2006) *Nat. Chem. Biol.* 2: 375-380; Mancini et al., (2008) *J. Am. Chem. Soc.* 130: 10836-10837; Miller et al., (2007) *Nat. Chem. Biol.* 3: 263-267). Of the few fluorescent probes tested in mouse models, none has been able to act systemically, but rather have been limited to local administration via intraperitoneal injection (Kundu et al., (2009) *Angew Chem. Int. Ed. Engl.* 48: 299-303; Lee et al., (2007) *Nat. Mater.* 6: 765-769; Oushiki et al., (2010) *J. Am. Chem. Soc.* 132: 2795-2801; Van de Bittner et al., (2010) *Proc. Natl. Acad. Sci. U.S.A.* 107: 21316-21321; Yuan et al., (2012) *J. Am. Chem. Soc.* 134: 1200-1211). While inflammation can often be localized to well-delineated regions of disease or injury, direct administration of probe is not always feasible and specific regions of inflammation are not necessarily known ab initio. Therefore, the inability of these probes to function after intravenous injection greatly constrains their utility to precisely identify inflammatory regions throughout the whole body and, as a result, fails to provide useful information for diagnosis of inflammation-related diseases and injury at the systemic level.

SUMMARY

For whole animal in-situ and real-time imaging of inflammation, a dual-color fluorescent nanoprobe (herein termed a "NanoDRONE") is provided for the detection of reactive oxygen and nitrogen species (RONS) in inflammatory microenvironments. Following systemic administration, the nanoprobes of the disclosure can act as molecular beacons of chemical mediators that initiate and propagate inflammatory diseases and injury. The nanoprobes of the disclosure are a RONS-responsive energy transferring nanosystem comprised of a fluorescent conjugated polymer core (energy donor) and a PEG-shell linked with RONS-sensing antennae as the FRET acceptor. By virtue of its biocompatible nanoarchitecture, the NanoDRONEs have rapid RONS response, good blood circulation properties and effective passive targeting to the leaky inflammatory microvasculature, enabling rapid accumulation and in-situ activation at inflammation sites. The nanoprobes of the disclosure allow in vivo imaging of the entire process of inflammation, from the release of local tissue distress signals that initiate the very early inflammatory cascade, to the action of leukocytes and macrophages late in the process of inflammation, through to restitution, providing a significant advance in whole-body diagnosis and monitoring of inflammatory diseases.

One aspect of the disclosure, therefore, encompasses embodiments of a composition comprising a nanoparticle probe, wherein said nanoparticle probe can comprise: (i) a nanoparticle core comprising a detectable signal emitter; and (ii) a quencher moiety, wherein the ability of the quencher to quench a signal from the emitter is substantially reduced on contact of the nanoparticle probe with a reactive oxygen and nitrogen species (RONS).

In embodiments of this aspect of the disclosure, the nanoparticle core can have a shell substantially surrounding the said nanoparticle core, wherein the shell can have the quencher linked thereto.

In embodiments of this aspect of the disclosure, the quencher can be linked to the detectable signal emitter by a linker cleavable by a reactive oxygen and nitrogen species (RONS).

In embodiments of this aspect of the disclosure, the quencher can be degradable by a reactive oxygen and nitrogen species (RONS).

In embodiments of this aspect of the disclosure, the nanoparticle core can comprise a superconducting polymer.

In these embodiments of this aspect of the disclosure, the superconducting polymer can be selected from the group consisting of: Poly[2-methoxy-5-(2-ethylhexyl-oxy)-1,4- phenylene-vinylene], Poly[2-methoxy-5-(2-ethylhexyloxy)-1,4-(1-cyanovinylene-1,4-phenylene)]; Poly[(9,9-dioctyl-2,7-divinylenefluorenylene)-alt-co-(9,10-anthracene)], Poly[{9,9-dihexyl-2,7-bis(1-cyanovinylene)fluorenylene}-alt-co-{2,5-bis(N,N'-diphenylamino)-1,4-phenylene}], Poly[(9,9-dioctylfluorenyl-2,7-diyl)-alt-(benzo[2,1,3]thiadiazol-4,7-diyl)], Poly[2,7-(9,9-di-octyl-fluorene)-alt-4,7-bis(thiophen-2-yl)benzo-2,1,3- thiadiazole], Poly[2,6-(4,4'-bis(2-ethylhexyl)dithieno[3,2-b:2',3'-d]silole)-alt-4,7(2,1,3-benzothiadiazole)], Poly[2,7-(9,9-di-octyl-fluorene)-alt-4,7-bis(thiophen-2-yl)benzo-2,1,3-thiadiazole], Poly[N-9'-heptadecanyl-2,7-carbazole-alt-5,5-(4',7'-di-2-thienyl-2',1',3'-benzothiadiazole)], Poly[3-hexylthiophene-2,5-diyl], and Poly[2,5-bis(3-dodecylthiophen-2-yl)thieno[3,2-b]thiophene].

In embodiments of this aspect of the disclosure, the detectable signal emitter can be a fluorophore and the signal emitted therefrom is quenched by FRET to the quencher.

In embodiments of this aspect of the disclosure, the nanoparticle probe can be an $NH_2$-functionalized conjugated polymer nanoparticle ($NH_2$-CPN) comprising a core nanoparticle comprising: poly[9,9'-dihexyl-2,7-bis(1-cyanovinylene)fluorenylene-alt-co-2,5-bis(N,N'-diphenylamino)-1,4-phenylene] (PCFDP) and the hydrophobic lipid tails of 1,2-Dimyristoyl-sn-glycero-3-phosphoethanolamine-N-[methoxy(polyethylene glycol)-2000] (DSPE-PEG) and 1,2-distearoyl-sn-glycero-3-phosphoethanolamine-N-[amino(polyethylene glycol)-2000] (DSPE-PEG-$NH_2$), whereby the N-[methoxy(polyethylene glycol)-2000] domain of the DSPE-PEG, and the N-[amino(polyethylene glycol)-2000] domain of the DSPE-PEG-$NH_2$ comprise the shell substantially surrounding the core nanoparticle; and the dye (IR-775-COOH) conjugated to the shell.

In embodiments of this aspect of the disclosure, the composition can further comprise a pharmaceutically acceptable carrier.

Another aspect of the disclosure encompasses embodiments of a method of detecting a site of inflammation in a human or non-human animal subject, the method comprising the steps of: (a) administering to a human or non-human subject a pharmaceutically acceptable composition comprising a population of nanoparticle probes wherein said nanoparticle probes can each comprise: (i) a nanoparticle core comprising a detectable signal emitter; and (ii) a quencher moiety, wherein the ability of the quencher to quench a signal from the emitter is substantially reduced on contact of the nanoparticle probe with a reactive oxygen and nitrogen species (RONS); (b) allowing the nanoparticle probes of the administered pharmaceutically acceptable composition to contact a site of inflammation in the subject animal or human; (c) generating a detectable signal from the detectable signal emitter; (d) detecting the signal emitted from the detectable signal emitter; and (e) locating the position of the detectable signal relative to the anatomy of the human or non-human animal subject, thereby identifying a site of inflammation in the human or non-human animal subject.

In embodiments of this aspect of the disclosure, the pharmaceutically acceptable composition can be administered to the human or non-human animal subject topically, intravenously, intraperitoneally, or by injection to a site suspected of being inflamed.

In embodiments of this aspect of the disclosure, the nanoparticle core can have a shell substantially surrounding the said nanoparticle core, wherein the shell can have the quencher linked thereto.

In embodiments of this aspect of the disclosure, the quencher can be linked to the detectable signal emitter by a linker cleavable by a reactive oxygen and nitrogen species (RONS).

In embodiments of this aspect of the disclosure, the quencher can be degradable by a reactive oxygen and nitrogen species (RONS).

In embodiments of this aspect of the disclosure, the nanoparticle core can comprise a superconducting polymer.

In these embodiments of this aspect of the disclosure, the superconducting polymer can be selected from the group consisting of: Poly[2-methoxy-5-(2-ethylhexyl-oxy)-1,4-phenylene-vinylene], Poly[2-methoxy-5-(2-ethylhexyloxy)-1,4-(1-cyanovinylene-1,4-phenylene)]; Poly[(9,9-dioctyl-2,7-divinylenefluorenylene)-alt-co-(9,10-anthracene)], Poly[{9,9-dihexyl-2,7-bis(1-cyanovinylene)fluorenylene}-alt-co-{2,5-bis(N,N'-diphenylamino)-1,4-phenylene}], Poly[(9,9-dioctylfluorenyl-2,7-diyl)-alt-(benzo[2,1,3]thiadiazol-4,7-diyl)], Poly[2,7-(9,9-di-octyl-fluorene)-alt-4,7-bis(thiophen-2-yl)benzo-2,1,3- thiadiazole], Poly[2,6-(4,4'-bis(2-ethylhexyl)dithieno[3,2-b:2',3'-d]silole)-alt-4,7(2,1,3-benzothiadiazole)], Poly[2,7-(9,9-di-octyl-fluorene)-alt-4,7-bis(thiophen-2-yl)benzo-2,1,3-thiadiazole], Poly[N-9'-heptadecanyl-2,7-carbazole-alt-5,5-(4',7'-di-2-thienyl-2',1',3'-benzothiadiazole)], Poly[3-hexylthiophene-2,5-diyl], and Poly[2,5-bis(3-dodecylthiophen-2-yl)thieno[3,2-b]thiophene].

In embodiments of this aspect of the disclosure, the detectable signal emitter can be a fluorophore and the signal emitted therefrom is quenched by FRET to the quencher.

In embodiments of this aspect of the disclosure, the nanoparticle probe can be an $NH_2$-functionalized conjugated polymer nanoparticle ($NH_2$-CPN) comprising a core nanoparticle comprising: poly[9,9'-dihexyl-2,7-bis(1-cyanovinylene)fluorenylene-alt-co-2,5-bis(N,N'-diphenylamino)-1,4-phenylene] (PCFDP) and the hydrophobic lipid tails of 1,2-Dimyristoyl-sn-glycero-3-phosphoethanolamine-N-[methoxy(polyethylene glycol)-2000] (DSPE-PEG) and 1,2-distearoyl-sn-glycero-3- phosphoethanolamine-N-[amino(polyethylene glycol)-2000] (DSPE-PEG-$NH_2$), whereby the N-[methoxy(polyethylene glycol)-2000] domain of the DSPE-PEG, and the N-[amino(polyethylene glycol)-2000] domain of the DSPE-PEG-$NH_2$ comprise the shell substantially surrounding the core nanoparticle; and the dye (IR-775-COOH) conjugated to the shell.

In embodiments of this aspect of the disclosure, the detectable signal emitter of the nanoparticle probe can be a fluorophore, and wherein the step (c) can comprise irradiating the human or non-human animal subject, or a tissue thereof, with an incident radiation inducing fluorescence by the fluorophore.

BRIEF DESCRIPTION OF THE DRAWINGS

Many aspects of the disclosure can be better understood with reference to the following drawings.

FIG. 1A schematically illustrates the preparation of $NH_2$-CPN and NanoDRONE, and the molecular structures of PCFDP, DSPE-PEG, DSPE-PEG-$NH_2$ and IR-775-COOH.

FIG. 1B is a digital image showing a TEM image of $NH_2$-CPN

FIG. 1C is a digital image showing a TEM image of a NanoDRONE nanoprobe.

FIG. 1D is a graph illustrating the DLS profiles of $NH_2$-CPN and a NanoDRONE in 1×PBS (pH=7.4).

FIG. 1E is a graph illustrating the UV-vis absorption of $NH_2$-CPN and a NanoDRONE in PBS (30 mM, pH=7.4).

FIG. 1F is a graph illustrating the PL spectra of $NH_2$-CPN and NanoDRONE in PBS (30 mM, pH=7.4).

FIG. 2A illustrates PL spectra of NanoDRONEs in PBS (30 mM, pH=7.4) in the absence or presence of nitric oxide (NO) with concentrations ranging from 0 to 0.6 μM NO in intervals of 0.1 μM.

FIG. 2B is a graph illustrating fluorescence responses of NanoDRONEs toward RONS in 1×PBS (pH=7.4) or FBS-containing 1×PBS (20 vol %, pH=7.4). F and $F_0$ are the PL intensities at $\lambda_{em}$=678 nm in the presence and absence of RONS, respectively. NanoDRONE concentration=0.1 μg/mL based on PCFDP; excitation at 405 nm.

FIG. 2C shows as series of digital images showing in vitro detection of endogenous NO. Fluorescence (top row) and DIC images (bottom row) of living murine macrophages (RAW 264.7). Cells were incubated with NanoDRONEs for 3 h before imaging. Panel (i): non-treated cells; Panel (ii): cells pretreated with lipopolysaccharide (LPS) for 12 h, and Panel (iii): cells pretreated with LPS for 10 h followed with PTIO for 2 h. NanoDRONE concentration=1.5 μg/mL; LPS concentration=1 μg/mL; PTIO concentration=1 μg/mL. Scale bar: 30 μm.

FIGS. 3A-3G illustrate the evaluation of NanoDRONEs in mouse models of bacterial and sterile inflammation.

FIG. 3A is a series of digital images showing NanoDRONE activation evaluated in mouse models of LPS-induced peritonitis. LPS was administered intraperitoneally either alone (Panels (i) and (ii)) or (Panel (iii)) with the NO scavenger PTIO, followed 4 h later by i.p. administration of saline (n=4) (Panel (i)), NanoDRONEs (n=4) (Panel (ii)), and NanoDRONEs with PTIO (n=4) (Panel (iii)), after which time fluorescence images were acquired.

FIG. 3B is a graph illustrating the average fluorescence intensity of the peritoneal cavity quantified for each treatment group shown in FIG. 3A. * indicates statistically significant increase of fluorescence intensity relative to all other groups (p<0.05).

FIG. 3C is a series of digital images illustrating NanoDRONEs administered intravenously to mice with spontaneous C. bovis infections. Fluorescence imaging was performed over time (n=2), showing activated and non-activated NanoDRONEs. Enlargements of the regions indicated by dashed white boxes are given below each corresponding image.

FIG. 3D shows following deconvolution of activated (dark) and non-activated (light) NanoDRONE fluorescence, the total signal from the whole animal quantified over time, identifying a biphasic mechanism of probe action, as indicated above the plot: accumulation (increase in non-activated probe) and activation (increase in activated probe). † indicates a significantly different change in fluorescence evolution over time between non-activated and activated nanoprobe (p<0.05).

FIG. 3E is a series of digital images showing, following the administration of NanoDRONE intravenously, mouse pina injured by ear hole punch, and fluorescent images acquired in real time (n=4) showing activated (dark) and non-activated (light) NanoDRONEs.

FIG. 3F is graph showing, following deconvolution of activated (dark) from non-activated (light) nanoprobe spectra, total mouse ear fluorescence quantified, reconfirming the biphasic mechanism of probe action, as shown above the plot: accumulation (increase in non-activated probe, light bar) and activation (increase in activated probe, dark bar). † indicates significantly different fluorescence response between non-activated and activated nanoprobe over time (p<0.05).

FIG. 3G shows mouse pina injured by ear hole punch and then allowed to heal for 14 d (left ear) or 24 h (right ear) prior to the intravenous administration of NanoDRONEs, followed by fluorescence imaging (n=3) showing activated (dark) and non-activated (light) nanoparticles.

FIG. 4A illustrates the microenvironmental changes in RONS concentrations during (i) early inflammation (transcription independent), (ii) late inflammation (transcription dependent), and (iii) following restitution. The legend in top left corner identifies biological and probe species represented in the cartoon.

FIG. 4B shows a series of digital images illustrating a histological analysis of the pina surrounding the hole punch tissue trauma (location indicated by white dashed arch) to identify the different phases of inflammation detectable by NanoDRONEs. Hematoxylin and eosin staining (Panels (i), (iii), and (v)) show tissue level changes consistent with (i) early inflammation (30 min), showing normal epidermal thickness, (iii) late inflammation (24 h), showing acanthosis and neutrophil infiltration (*); and (v) restitution (14 d), showing maintained acanthosis and fibrous scar tissue (s). Corresponding unstained, paraffin-embedded tissue sections (Panels (ii), (iv), and (vi)) show the extent and location of accumulation of NanoDRONE around the site of injury.

FIG. 15A is a series of digital images showing, for the purpose of quantitation, the fluorescence from activated (top) and non-activated (bottom) NanoDRONEs deconvolved following hyperspectral imaging.

FIG. 15B is a series of digital images of a histological analysis of hematoxylin and eosin-stained sections of uninfected (left top) and infected (right top) skin show characteristic differences related to infection by *C. bovis*. Thickening of the epidermis (white †) indicates acanthosis consistent with infection, relative to normal epidermal thickness. In addition, neutrophil invasion (*), loss of mast cells (+), and orthokeratotic hyperkeratosis (arrows) are also consistent with infection by *C. bovis*. Unstained, paraffin-embedded samples of normal (bottom left) and infected skin (bottom right) show differential distribution of NanoDRONEs within the tissues, with the probe remaining in the vasculature of normal tissue, but spreading out into the dermal layers in areas of infection.

Figure 1A:
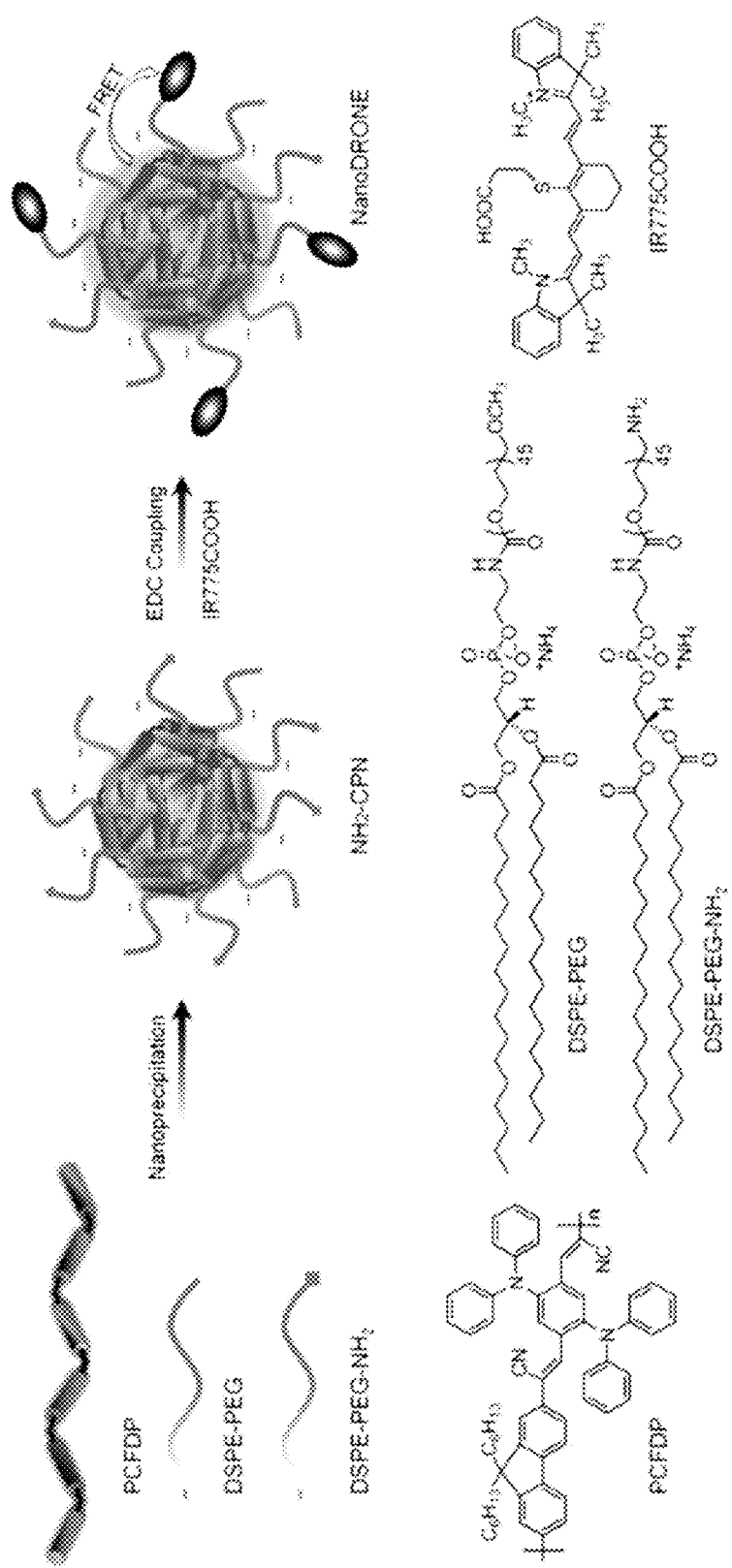
FIGS. 1A-1F illustrate the synthesis and characterization of the nanoprobes of the disclosure.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

DEFINITIONS

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "reactive oxygen and nitrogen species (RONS)" as used herein refers to an oxygen- or nitrogen-containing molecules that are capable of producing oxidative damage to other molecules. Many, but not all, RONS are free radicals. A radical is a group of atoms which behaves as a unit and has one or more unpaired electrons. Examples include, but are not limited to: $H_2O_2$ (hydrogen peroxide), $*O_2^-$ (superoxide radical), $*OH$, (hydroxyl radical), $ONOO^-$ (peroxynitrite), $O_2^1$ (singlet oxygen), $O^3$ (ozone), $*NO$ (nitric oxide), and $*NO^2$ (nitrogen dioxide).

The term "nanoparticle" as used herein refers to a particle having a diameter of between about 1 and about 1000 nm. Similarly, by the term "nanoparticles" is meant a plurality of particles having an average diameter of between about 1 and about 1000 nm.

The terms "core" or "nanoparticle core" as used herein refers to the inner portion of nanoparticle. A core can substantially include a single homogeneous monoatomic or polyatomic material. A core can be crystalline, polycrystalline, or amorphous. A core may be "defect" free or contain a range of defect densities. In this case, "defect" can refer to any crystal stacking error, vacancy, insertion, or impurity entity (e.g., a dopant) placed within the material forming the core. Impurities can be atomic or molecular.

In particular, it is understood that the nanoparticle core of the compositions of the disclosure can comprise a superconducting polymer that may emit a fluorescent light when irradiated by a suitable incident energy. The superconducting polymers suitable for use in the compositions of the disclosure may include, but are not limited to, such as Poly(phenylene-vinylene) (PPV) Derivatives: Poly[2-methoxy-5-(2-ethylhexyl-oxy)-1,4-phenylene-vinylene], Poly[2-methoxy-5-(2-ethylhexyloxy)-1,4-(1-cyanovinylene-1,4-phenylene)]; Polyfluorene (PF) Derivatives: Poly[(9,9-dioctyl-2,7-divinylenefluorenylene)-alt-co-(9,10-anthracene)], Poly[{9,9-dihexyl-2,7-bis(1-cyanovinylene)fluorenylene}-alt-co-{2,5-bis(N,N'-diphenylamino)-1,4-phenylene}], Poly[(9,9-dioctylfluorenyl-2,7-diyl)-alt-(benzo[2,1,3]thiadiazol-4,7-diyl)], Poly[2,7-(9,9-di-octyl-fluorene)-alt-4,7-bis(thiophen-2-yl)benzo-2,1,3-thiadiazole], Poly[2,6-(4,4'-bis(2-ethylhexyl)dithieno[3,2-b:2',3'-d]silole)-alt-4,7(2,1,3-benzothiadiazole)], Poly[2,7-(9,9-di-octyl-fluorene)-alt-4,7-bis(thiophen-2-yl)benzo-2,1,3-thiadiazole], Poly[N-9'-heptadecanyl-2,7-carbazole-alt-5,5-(4',7'-di-2-thienyl-2',1',3'-benzothiadiazole)], Polythiophene (PT) derivatives: Poly[3-hexylthiophene-2,5-diyl], Poly[2,5-bis(3-dodecylthiophen-2-yl)thieno[3,2-b]thiophene] and the like.

Nanoparticles of the disclosure may further comprise a "coat" or "shell" of a second material that surrounds the core. A coat can include a layer of material, either organic or inorganic, that covers or substantially covers the surface of the core of a nanoparticle. A coat may be crystalline, polycrystalline, or amorphous or may comprise, for example, hydrophilic regions of a molecule where hydrophobic regions thereof are either conjugated to are integral to the underlying nanoparticle core.

A coat or shell may be "complete", indicating that the coat substantially or completely surrounds the outer surface of the core (e.g., substantially all surface atoms of the core are covered with coat material). Alternatively, the coat may be "incomplete" such that the coat partially surrounds the outer surface of the core (e.g., partial coverage of the surface core atoms is achieved). In addition, it is possible to create coats of a variety of thicknesses, which can be defined in terms of the number of "monolayers" of coat material that are bound to each core. A "monolayer" is a term known in the art referring to a single complete coating of a material (with no additional material added beyond complete coverage). Incomplete monolayers may be either homogeneous or inhomogeneous, forming islands or clumps of coat material on the surface of the nanoparticle core. Coats may be either uniform or non-uniform in thickness. In the case of a coat having non-uniform thickness, it is possible to have an "incomplete coat" that contains more than one monolayer of coat material. A coat may optionally comprise multiple layers of a plurality of materials in an onion-like structure, such that each material acts as a coat for the next-most inner layer. Between each layer there is optionally an interface region. The term "coat" as used herein describes coats formed from substantially one material as well as a plurality of materials that can, for example, be arranged as multi-layer coats.

It will be understood by one of ordinary skill in the art that when referring to a population of nanoparticles as being of a particular "size", what is meant is that the population is made up of a distribution of sizes around the stated "size". Unless otherwise stated, the "size" used to describe a particular population of nanoparticles will be the mode of the size distribution (i.e., the peak size). By reference to the "size" of a nanoparticle is meant the length of the largest straight dimension of the nanoparticle. For example, the size of a perfectly spherical nanoparticle is its diameter.

The term "FRET" as used herein refers to fluorescence resonance energy transfer between molecules. In FRET methods, one fluorophore is able to act as an energy donor and the other of which is an energy acceptor molecule. These are sometimes known as a reporter molecule and a quencher molecule respectively. The donor molecule is excited with a specific wavelength of light for which it will normally exhibit a fluorescence emission wavelength. The acceptor molecule is also excited at this wavelength such that it can accept the emission energy of the donor molecule by a variety of distance-dependent energy transfer mechanisms. Generally the acceptor molecule accepts the emission energy of the donor molecule when they are in close proximity (e.g., on the same, or a neighboring molecule). FRET techniques are well known in the art, and can be readily used to detect the titanium oxide-bound peptides of the present disclosure. See for example U.S. Pat. Nos. 5,668,648, 5,707,804, 5,728,528, 5,853,992, and 5,869,255 (for a description of FRET dyes), T Mergny et al., (1994) Nucleic Acid Res. 22:920-928, and Wolf et al., (1988) Proc. Natl. Acad. Sci. USA 85:8790-8794 (for general descriptions and methods for FRET), each of which is hereby incorporated by reference in its entirety.

The term "fluorophore" as used herein refers to a component of a molecule that causes a molecule to be fluorescent. It is a functional group in a molecule which will absorb energy of a specific wavelength and re-emit energy at a different (but equally specific) wavelength. The amount and wavelength of the emitted energy depend on both the fluorophore and the chemical environment of the fluorophore. Fluorophores for use in the compositions of the disclosure include, but are not limited to, fluorescein isothiocyanate (FITC), a reactive derivative of fluorescein, which has been one of the most common fluorophores chemically attached to other, non-fluorescent, molecules to create new fluorescent molecules for a variety of applications. Other historically common fluorophores are derivatives of rhodamine (TRITC), coumarin, and cyanine. Newer generations of fluorophores such as the ALEXA FLUORS® and the DYLIGHT FLUORS® are generally more photostable, brighter, and less pH-sensitive than other standard dyes of comparable excitation and emission.

The term "dye" as used herein refers to any reporter group whose presence can be detected by its light absorbing or light emitting properties. For example, Cy5 is a reactive water-soluble fluorescent dye of the cyanine dye family. Cy5 is fluorescent in the red region (about 650 to about 670 nm). It may be synthesized with reactive groups on either one or both of the nitrogen side chains so that they can be chemically linked to either nucleic acids or protein molecules. Labeling is done for visualization and quantification purposes. Cy5 is excited maximally at about 649 nm and emits maximally at about 670 nm, in the far red part of the spectrum; quantum yield is 0.28. FW=792. Suitable fluorophores(chromes) for the probes of the disclosure may be selected from, but not intended to be limited to, fluorescein isothiocyanate (FITC, green), cyanine dyes Cy2, Cy3, Cy3.5, Cy5, Cy5.5 Cy7, Cy7.5 (ranging from green to near-infrared), Texas Red, and the like. Derivatives of these dyes for use in the embodiments of the disclosure may be, but are not limited to, Cy dyes (Amersham Bioscience), Alexa Fluors (Molecular Probes Inc.), HILYTE® Fluors (AnaSpec), and DYLITE® Fluors (Pierce, Inc).

The term "fluorescent acceptor molecule" as used herein refers to any molecule that can accept energy emitted as a result of the activity of a bioluminescent donor protein, and re-emit it as light energy.

The terms "fluorescence quencher" or "quencher" as used herein refer to a molecule that interferes with the fluorescence emitted by a fluorophore or bioluminescent polypeptide. This quencher can be selected from non-fluorescent aromatic molecules, to avoid parasitic emissions. Exemplary quenchers include, but are not limited to, Dabsyl or a BLACK HOLE QUENCH ER® that are non-fluorescent aromatic molecules that prevent the emission of fluorescence when they are physically near a fluorophore. The quencher can also be, but is not limited to, a fluorescent molecule, for example TAMRA (carboxytetramethylrhodamine). A particularly advantageous quencher suitable for use in the compositions of the disclosure is a modified dye such as IR-775-COOH. When the quencher is a fluorescent dye, its fluorescence wavelength is typically substantially different from that of the reporter dye.

The terms "quench" or "quenches" or "quenching" or "quenched" as used herein refer to reducing the signal produced by a molecule. It includes, but is not limited to, reducing the signal produced to zero or to below a detectable limit. Hence, a given molecule can be "quenched" by, for example, another molecule and still produce a detectable signal, albeit the size of the signal produced by the quenched molecule can be smaller when the molecule is quenched than when the molecule is not quenched.

The term "inflammatory disease" as used herein refers to, but is not limited to, autoimmune diseases such as arthritis, rheumatoid arthritis, multiple sclerosis, systemic lupus erythematosus, other diseases such as asthma, psoriasis, inflammatory bowel syndrome, neurological degenerative diseases such as Alzheimer's disease, Parkinson's disease, Huntington's disease, vascular dementia, and other pathological conditions such as epilepsy, migraines, stroke and trauma. The term "inflammation" as used herein further refers to physiological or pathophysiological conditions including, but not limited to, a physical or mechanical trauma, blood vessel infarction, and the like that may generate RONS detectable by the nanoparticles herein disclosed.

By the term "detectable signal emitter" is meant, for the purposes of the specification or claims, a label molecule that is incorporated indirectly or directly into a nanoparticle, wherein the label molecule facilitates the detection of the nanoparticle in which it is incorporated, for example when the nanoparticle of the disclosure is at a site of inflammation and activated by interaction between the nanoparticle or the quencher component thereof and a RONS. Thus, "detectable signal emitter" is used synonymized with "label molecule".

The term "NH$_2$-functionalized conjugated polymer" as used herein refers to a nanoparticle formed by co-condensing one or more types of monomer to form a polymer and wherein on the outer surface of said nanoparticle are located amine groups that are available for conjugating with another molecular entity that may have such as a reactive carboxyl group thereon.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

Abbreviations

NanoDRONE: Nanoprobe for the Detection of reactive Oxygen and Nitrogen Species; RONS: Reactive Oxygen and Nitrogen Species; BRET: Bioluminescence Resonance energy transfer imaging; FRET: Förster (or Fluorescence) Resonance Energy Transfer; PBS: phosphate-buffered saline; CPN: conjugated polymer nanoparticles; PCFDP: poly[9,9'-dihexyl-2,7-bis(1-cyanovinylene)fluorenylene-alt-co-2,5-bis(N,N'-diphenylamino)-1,4-phenylene]; DSPE-PEG: 1,2-Dimyristoyl-sn-glycero-3-phosphoethanolamine-N-[methoxy(polyethylene glycol)-2000]; DSPE-PEG-NH2: 1,2-distearoyl-sn-glycero-3-phosphoethanolamine-N-[amino(polyethylene glycol)-2000]; PL: photoluminescence; PTIO: NO scavenger 2-(4-carboxyphenyl)-4,5-dihydro-4,4,5,5-tetramethyl-1H-imidazolyl-1-oxy-3-oxide (carboxy-PTIO); LPS: lipopolysaccharide.

Description

Despite the significance of inflammation in injury, bacterial infection and disease, whole-body high temporal resolution imaging of inflammation has yet to be achieved. The present disclosure encompasses embodiments of a dual-color fluorescent nanoprobe for real-time, whole-body in situ detection of integral pro-inflammatory chemical mediators, reactive oxygen and nitrogen species (RONS). The nanoprobe(s) of the disclosure possesses a spectral fingerprint that instantly changes upon probe activation, providing qualitative detection of RONS activity via hyperspectral deconvolution technology, and long blood circulation and passive targeting to the leaky inflammatory microvasculature for intelligent localization to inflammatory regions independent of their cause. These features enable the in vivo imaging of the complete progression of inflammation from subclinical time points prior to histological changes, through to restitution, and are advantageous for the diagnosis of inflammatory diseases as well as, but not limited to, any physiological or pathological condition that may generate reactive oxygen and nitrogen species. The nanoprobes of the disclosure are useful as a platform for systemic, in situ and real-time imaging of microenvironmental changes associated with pathological processes.

Reactive oxygen and nitrogen species (RONS) play important roles in many biological processes, including for example, inflammation or a mechanical or other pathological condition of a tissue. Inflammation is a key component of many pathophysiological processes ranging from acute inflammation associated with sterile or ischemic/reperfusion injury, to chronic inflammation in responses to such as bacterial infection, tumor growth, cardiovascular disease, arthritis, and the like. The present disclosure provides embodiments of RONS-responsive fluorescent conjugated polymer nanoparticles suitable for sensing microenvironments of inflammation, and when in those inflammatory regions to turn on and act as a beacon for the in situ detection of inflammation. By identifying the location of inflammation, these nanoparticles can delineate the specific anatomical regions that have entered a pathophysiological state, and which could require therapeutic intervention.

The RONS-nanoprobes of the disclosure comprise a core-shell energy transferring architecture in which the energy acceptor is located at the surface of the nanoparticle, acting as both the quencher and a RONS-sensitive antenna.

The RONS-responsive nanoparticles of the disclosure are formed by a fundamentally two-step process. First, bare conjugated polymer nanoparticles can be, but are not exclusively, generated from the conjugated polymer 1,2-diasteroyl phosphatidyl ethanolamine poly(ethylene glycol), and 1,2-diasteroyl phosphatidyl ethanolamine poly(ethylene glycol) amine by nanoprecipitation. The hydrophobic conjugated polymers can then interact with hydrophobic poly(ethylene glycol) lipid tails which are incorporated into the nanoparticle, which is shielded by hydrophilic poly(ethylene glycol) chains. The synthesis method of the disclosure, as schematically shown in FIG. 1A, results in substantially mono-dispersed nanoparticles having hydrodynamic diameters less than about 100 nm.

In one embodiment of the methods of the disclosure, a quencher with a carboxyl reactive group can be synthesized from the dye IR-775 Chloride, and can then be covalently attached to the nanoparticle with the amine groups on the surface of bare conjugated-polymer nanoparticles surface through a carbodiimide-activated coupling reaction to generate a shell covering in total or in part the underlying nanoparticle core. Such a core-shell architecture allows for fluorescence resonance energy transfer (FRET) from the excited conjugated polymer core to the quencher at the nanoparticle surface, leading to the quenched fluorescence of the RONS-responsive nanoparticles as the initial state.

The IR-775-based quencher of the disclosure is sensitive to RONS (such as peroxynitrite, superoxide anion, nitric oxide, and hypochlorite) and undergoes oxidative decomposition. Accordingly, upon exposure to RONS the quenching of the FRET is lessened or abolished and the conjugated polymer nanoparticle switches from a non-fluorescent (quenched) state to a fluorescence-emitting state, resulting in a detectable fluorescent signal for real-time systemic localization of RONS.

One hallmark of inflammation is enhanced vascular permeability at the site of pathophysiology early in the inflammatory process, which accounts for the redness and swelling that is often observed. The enhanced permeability is due to vasodilation and increased fluid accumulation induced by chemical mediators released by resident tissue mast cells and macrophages upon stimulation by bacterial antigens or endogenous signals of tissue destruction (e.g. lipid autacoids). The immediate response of these first-line inflammatory mediator cells is to release cytokines and reactive oxygen and nitrogen species that reach nearby arterioles, capillaries, and venules, and initiate the inflammatory response. These released reactive oxygen and nitrogen species include the superoxide anion, nitric oxide, and peroxynitrite, all of which can degrade IR-775S-COOH and abolish the FRET-mediated quenching of the conjugated polymer nanoparticles of the disclosure. This early phase of inflammation can, therefore, be detected by the conjugated polymer nanoparticles of the disclosure, allowing for the detection of inflammation within the first 30 min of induction.

Hours after the onset of inflammation sees the arrival of neutrophils and non-resident macrophages, both of which can contribute to resolution of the cause of inflammation through the production of reactive oxygen and nitrogen species, including nitric oxide, superoxide anion, peroxynitrite, and hypochlorite. Since the production of reactive oxygen and nitrogen species persists through this later, leukocyte-mediated phase of inflammation, the conjugated polymer nanoparticles of the disclosure are also advantageous for the detection of late stages of inflammation.

Due to their small size (between about 50 and about 100 nm after IR-775S-COOH conjugation), good stability and biocompatibility, the conjugated nanoparticles of the disclosure exhibit protracted systemic circulation and can accumulate at sites of inflammation due to the vascular leakiness inherent to this pathological condition. Once accumulated at the sites of inflammation, the enhancement (up to about 1000-fold) in reactive oxygen and nitrogen species concentration characteristic of inflammatory microenvironments degrades the IR-775S-COOH, abolishing the FRET-mediated quenching of the conjugated polymer nanoparticle. Upon excitation of the animal with the specific wavelength of light, only those conjugated polymer nanoparticles within inflammatory microenvironments and subjected to RONS-induced quencher degradation will emit near-infrared light and serve as a beacon signal for pathophysiology.

Inflammatory responses may be detected after systemic administration of the nanoparticles of the disclosure to a human or non-human animal subject and can, therefore, provide for whole body diagnosis of sites of inflammation relevant to a number of both acute and chronic medical conditions. For example, but not intended to be limiting, in sterile injury (tissue damage not induced by bacterial infection), and particularly for veterinary medicine where the patient cannot adequately communicate the sites of pain (but also usefully applied to humans), inflammation can be detected and located after systemic administration of the nanoparticle, potentially identifying areas of soft- and hard-tissue damage (torn ligaments, tendon damage, cartilage damage, fractures, etc.). The capability to see the sites of injury would be advantageous in avoiding the use of invasive exploratory procedures, reducing the time to diagnosis and onset of treatment. In humans, the determination of deep soft tissue damage due to sports injury/strenuous activity can be difficult and may be usefully obtained with the conjugated polymer nanoparticles of the disclosure.

The primary response to a bacterial infection is elicited through inflammation. The ability of the conjugated polymer nanoparticles of the disclosure to indirectly identify regions of infection by detecting the associated inflammatory response is useful in both assessing the degree and locations of infection, as well as monitoring treatment response to antibiotics by indicating whether or not previously identified areas of infection have decreased in severity or disappeared. Monitoring bacterial infection is relevant to both human and veterinary medicine.

Many diseases are associated with an inflammation response, including cancer, cardiovascular disease, and arthritis. The ability of the conjugated nanoparticles of the disclosure to be administered intravenously and their sensitivity to inflammatory microenvironments makes them suitable for use in whole body diagnostic imaging. In one aspect, the conjugated polymer nanoparticles of the disclosure can be administered intravenously to determine the location of a tumor due to the association of reactive oxygen and nitrogen species with tumor growth and physiology. In another aspect, the specific activation of the nanoparticle in the tumor tissue can assist in image-guided tumor resection, identifying the margins of the tumor to allow for more complete resection. Similarly, the nanoparticles may be applied to cardiovascular disease by both identifying regions of arteries that are atherosclerotic, and can aid in guiding the treatment of these regions by delimiting their boundaries.

The conjugated polymer nanoparticles of the disclosure have the advantages of enhanced biocompatibility and stability over currently available fluorescent probes intended for imaging reactive oxygen and nitrogen species. The components of the conjugated polymer nanoparticle are free from heavy metals that render other nanoparticle-based fluorophores unsuitable for medical use (e.g. quantum dots). In addition, the stability of the optical properties (i.e. quantum yield, photostability) of the conjugated polymer nanoparticle in biological environments is enhanced relative to small molecule fluorophores. The enhanced biocompatibility and stability of the conjugated polymer nanoparticles of the disclosure, therefore, allows them to be suitable for systemic administration.

The modular formulation of the conjugated polymer nanoparticle allows for the modification of its fluorescent, excitation, and microenvironmental sensing properties. For example, there are available other conjugated polymers and fluorophore dopants for tailoring production of conjugated polymer nanoparticles with varying emissive spectral properties (i.e. the emission color can be changed).

It is also contemplated that the surface of the nanoparticle can be readily modified with a bioluminescent polypeptide such as, but not limited to, a luciferase enzyme for luciferin-mediated bioluminescent resonance energy transfer (BRET), thereby eliminating the need for an external excitation source. It is further contemplated that administration of such a BRET-based nanoprobe of the disclosure may also require the co-administration of an agent such as coelenterazine for the activation of the luciferase activity. It is also within the scope of the present disclosure to incorporate a quenching agent that is selected to quench an energy emission generated by the selected energy emitter.

Synthesis and Characterization of NanoDRONEs: For example, but not intended to be limiting, the facile synthesis of the NanoDRONE nanoprobes of the disclosure may be by the two steps as illustrated in FIG. 1A. Nanoprecipitation methods (as described, for example, in Pecher & Mecking (2010) Chem. Rev. 110: 6260-6279 and Wu et al. (2011) Angew. Chem. Int. Ed. Engl. 50: 3430-3434, incorporated herein by reference in their entireties) can be used to prepare $NH_2$-functionalized conjugated polymer nanoparticles ($NH_2$-CPN). The nanoparticles can then be conjugated to entities such as a carboxyl-terminated dye (IR-775-COOH) through a carbodiimide-activated coupling reaction to form the NanoDRONE nanoparticles. During co-precipitation of three different polymers: poly[9,9'-dihexyl-2,7-bis(1-cyanovinylene)fluorenylene-alt-co-2,5-bis(N,N'-diphenylamino)-1,4-phenylene] (PCFDP), DSPE-PEG, and DSPE-PEG-$NH_2$ in water, collapse of heterogeneous polymer chains can occur, which in turn entraps the non-water soluble PCFDP chains and the hydrophobic lipid tails of DSPE-PEG and DSPE-PEG-$NH_2$. This hydrophobicity-driven self-assembly simultaneously forms the hydrophobic nanoparticle core and the biocompatible hydrophilic shell, orienting the PEG segments of DSPE-PEG and DSPE-PEG-$NH_2$ towards the aqueous environment.

Figure 5:
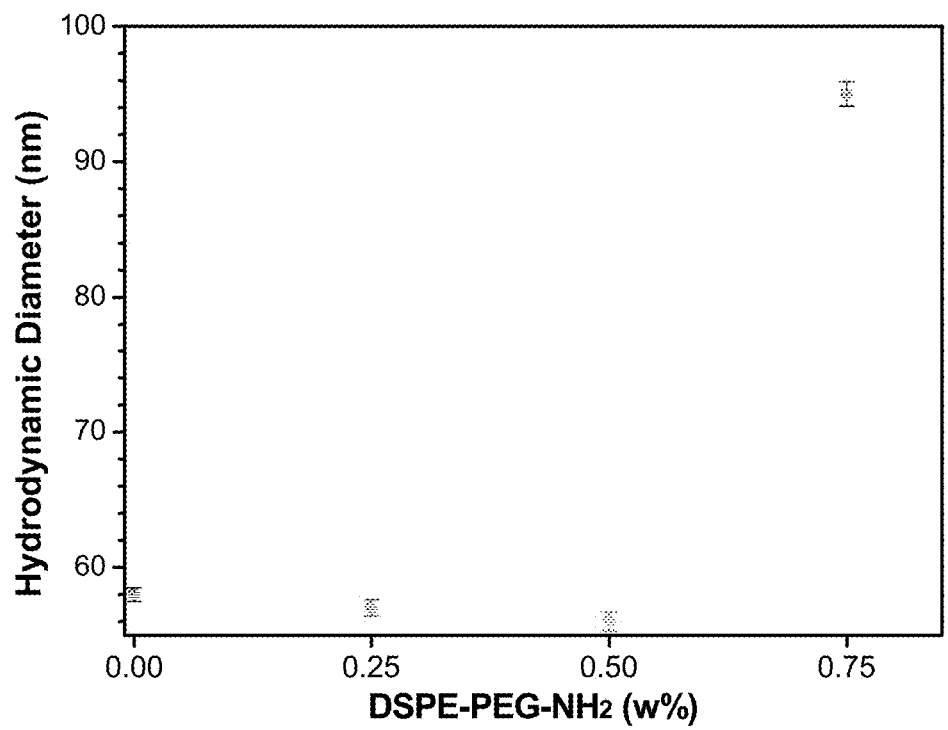
FIG. 5 is a graph illustrating the hydrodynamic diameters of $NH_2$-CPN in 1×PBS (pH=7.4) as a function of the weight percentage of DSPE-PEG-$NH_2$ in the lipids. Error bars indicate S.D.
Figure 6:
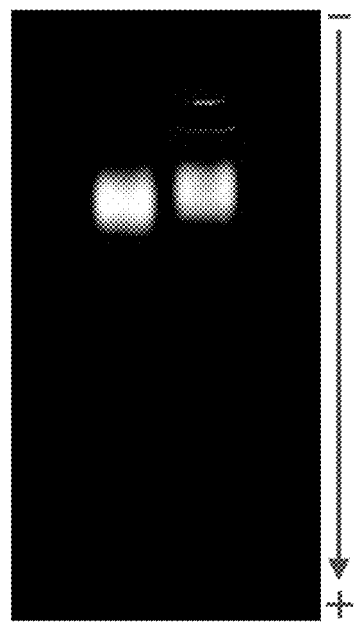
FIG. 6 is a digital image of agarose gel electrophoresis of $NH_2$-CPN and NanoDRONEs.

About 50% of DSPE-PEG-NH$_2$ in the total lipid (weight-by-weight) was found to be especially advantageous for the formulation; higher percentages can lead to nanoparticles with reduced stability and a larger size, as shown in FIG. 5. IR-775-COOH was subsequently conjugated to the surface of NH$_2$-CPN via a 1-ethyl-3-(3-dimethylaminopropyl)carbodiimide (EDC)-catalyzed coupling reaction, ultimately affording NanoDRONEs. The successful conjugation of surface fluorophore was confirmed by agarose gel electrophoresis (FIG. 6), showing that the additional surface positive charges afforded by the fluorophore caused NanoDRONEs to migrate to a lesser extent than the more anionic NH$_2$-CPN.

Figure 1B:
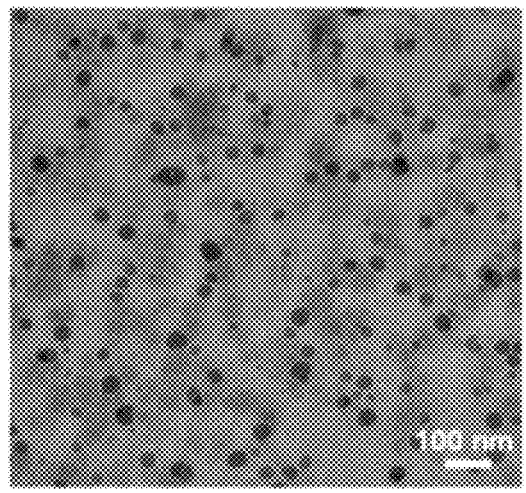
Figure 1C:
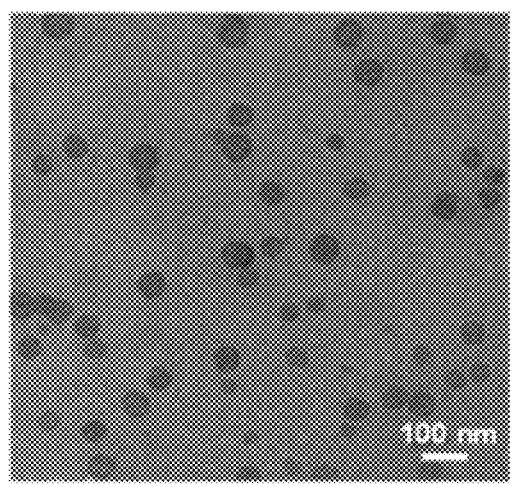
Figure 1D:
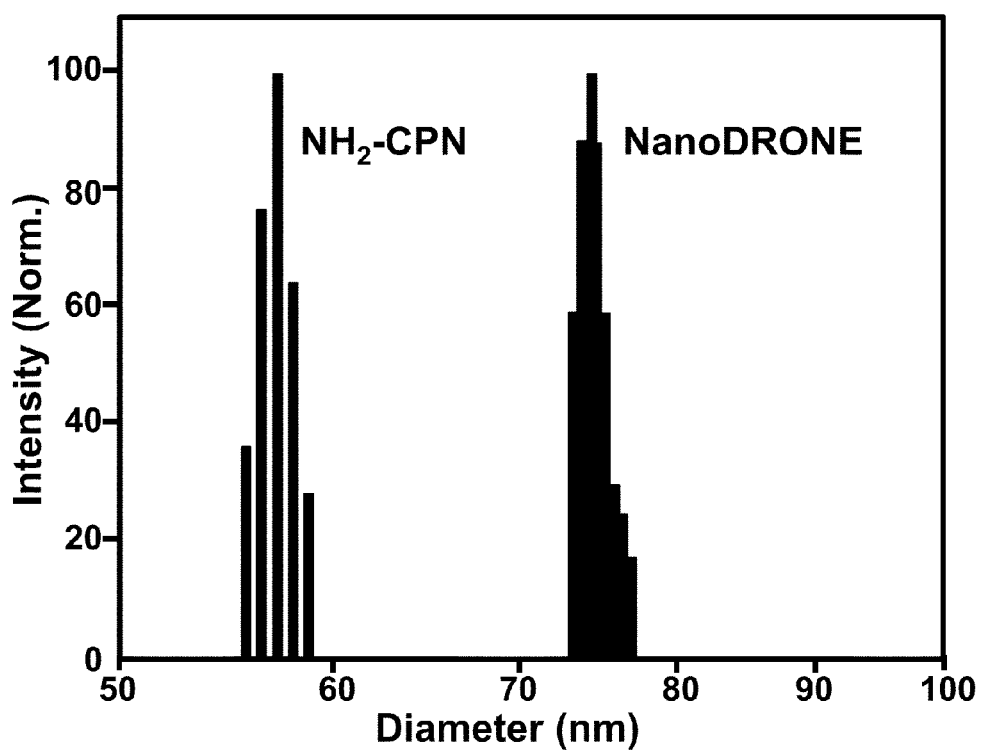

The general physical properties of the exemplary NanoDRONE nanoprobes of the disclosure were evaluated in comparison to the nanoparticle precursor (NH$_2$-CPN). As shown in FIGS. 1B and 1C, TEM images indicated that both NH$_2$-CPN and NanoDRONEs have spherical morphologies with respective average diameters of about 45 nm and about 52 nm, correlating with mean hydrodynamic diameters of 56±0.7 nm and 78±0.8 nm, respectively, as measured by dynamic light scattering. Both NH$_2$-CPN and the NanoDRONEs exhibit narrow polydispersities of 0.16±0.01 and 0.17±0.02, respectively. With the conjugation of positively-charged dye molecules to the nanoparticle surface, the zeta potential increased from −21±0.8 mV (NH$_2$-CPN) to −9±0.2 mV (NanoDRONEs) at pH=7.4.

Figure 1E:
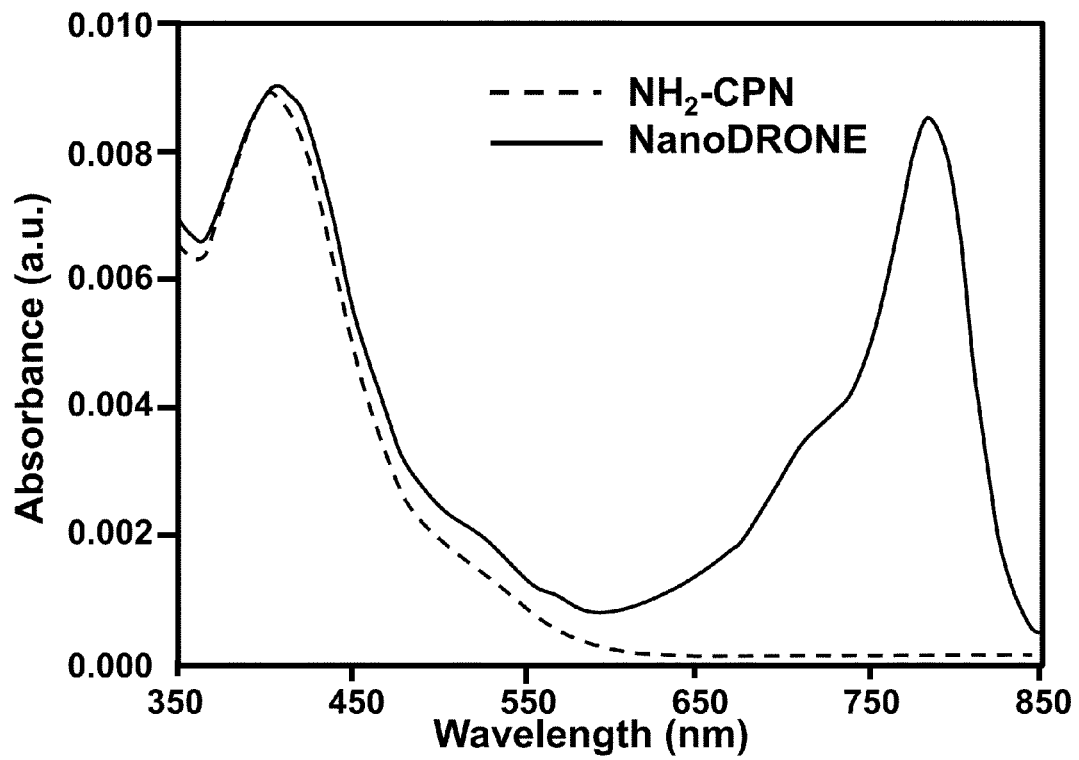
Figure 1F:
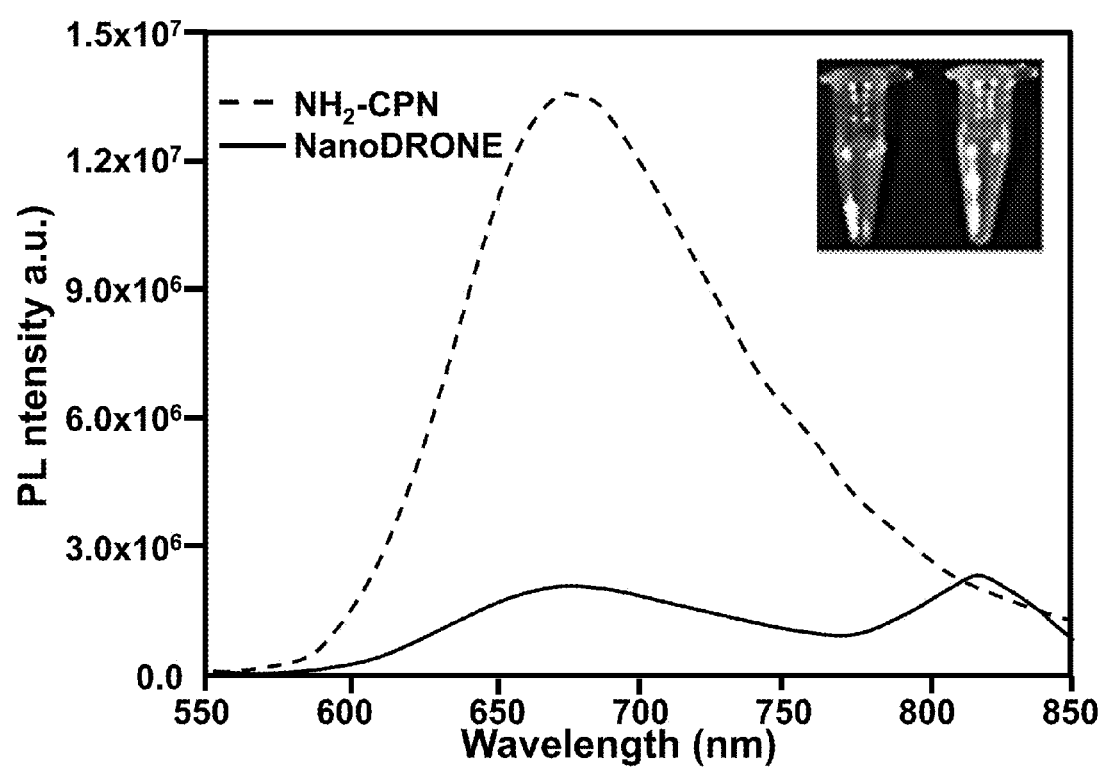
Figure 7:
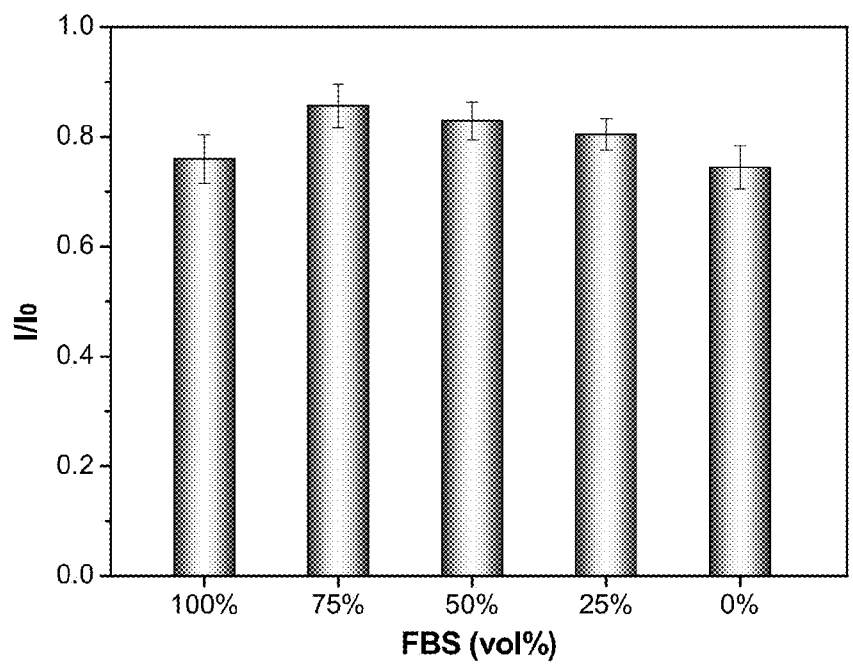
FIG. 7 is a graph illustrating the fluorescence stability of NanoDRONE under physiological relevant conditions. Fluorescence changes of NanoDRONE after incubation in FBS-containing 1×PBS (pH=7.4) at 37° C. for 24 h. I and $I_0$ stand for the PL intensities at 678 nm of NanoDRONE after (I) and before ($I_0$) incubation, respectively. NanoDRONE concentration=3 μg/mL. Excitation at 405 nm. Error bars are SD.

NanoDRONEs had extremely high stability in aqueous solution as shown in FIG. 7, attributable to the strong steric repulsion provided by the PEG shell. The spectroscopic characteristics of the nanoprobe (as shown in FIGS. 1E and 1F) demonstrate the unique dual-color spectral fingerprints that differentiate its activation states. Upon excitation of NanoDRONEs, the additional emission peak at 818 nm relative to NH$_2$-CPN indicated the occurrence of FRET from the nanoparticle core (energy donor) to the fluorophore (energy acceptor) on the surface. As compared to NH$_2$-CPN, NanoDRONEs emitted much weaker fluorescence (Inset of FIG. 1F): the photoluminescence (PL) quantum yield of the conjugated nanoparticle core dropped to 3% for NanoDRONEs from the original 18% of NH$_2$-CPN, further confirming efficient FRET within NanoDRONE. Therefore, the spectral fingerprint of the non-activated NanoDRONE comprises two emission peaks at 678/818 nm, while the activated one has a single emission peak at 678 nm due to the loss of the surface fluorophore after exposure to RONS. These RONS-dependent spectral fingerprints can, therefore, facilitate in vivo hyperspectral imaging of both NanoDRONE and its activation at inflammation sites.

Figure 2A:
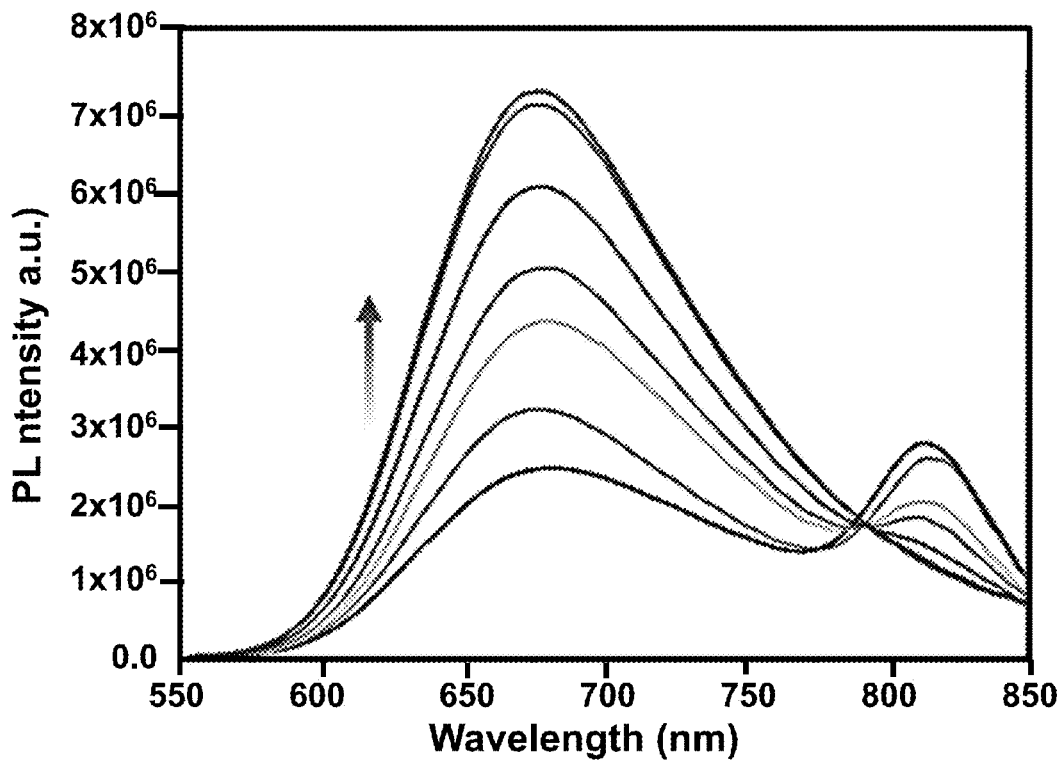
FIGS. 2A-2C illustrate the in vitro responses of a Nano-DRONE to RONS.

Evaluation of RONS Responsiveness of NanoDRONEs:

The fluorescence responses of NanoDRONEs toward RONS under physiological conditions in both 1×PBS and FBS-containing 1×PBS (pH=7.4) were evaluated. For example, FIG. 2A shows PL spectral changes of NanoDRONEs upon addition of a RONS such as NO. With increasing concentrations of NO, the nanoparticle core emission peak at 678 nm gradually increased with the concurrent loss of emission at 818 nm, exhibiting the instant change of its spectral fingerprint in response to NO. This was the result of the rapid oxidative cleavage of the central oligomethine linker of the FRET acceptor IR-775-COOH on the nanoparticle surface (Oushiki et al. (2010) *J. Am. Chem. Soc.* 132: 2795-2801), which abolished the FRET within NanoDRONEs and recovered donor fluorescence at 678 nm.

Figure 2B:
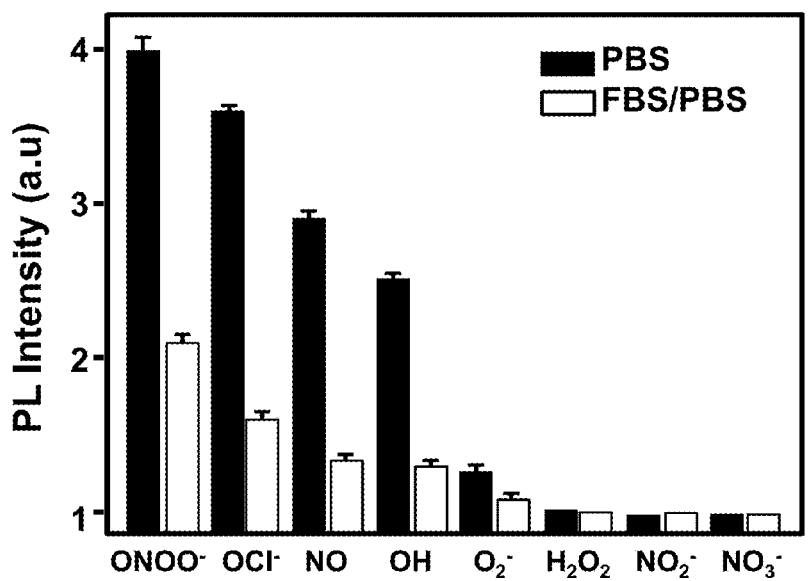
Figure 8:
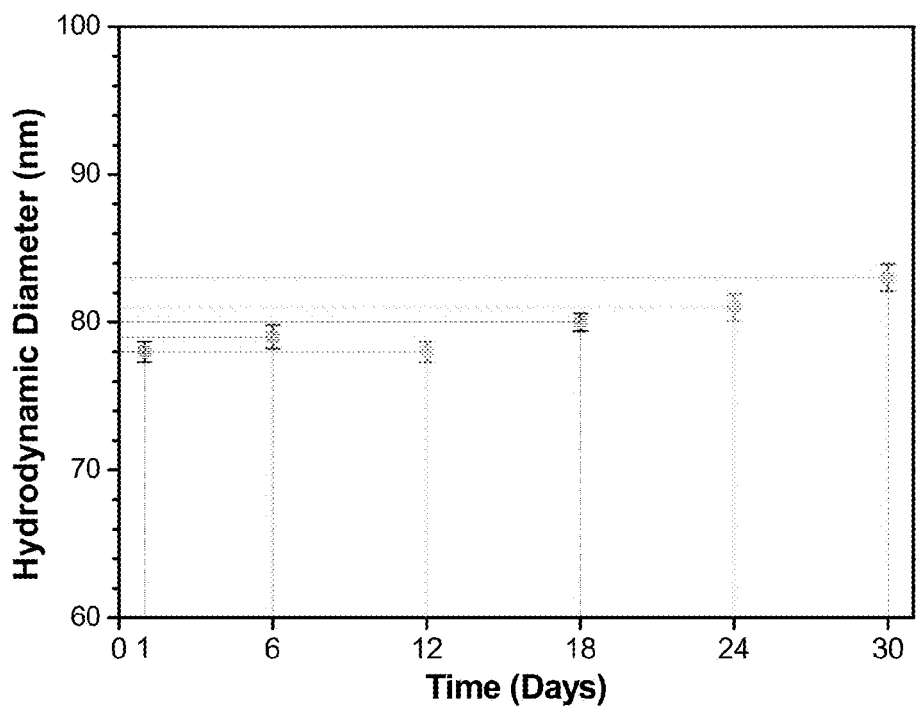
FIG. 8 is a graph illustrating the size stability study of NanoDRONE. Hydrodynamic diameter of NanoDRONE in 1×PBS (pH=7.4) as a function of time. Error bar indicates SD.

As summarized in FIG. 2B, the discriminatory fluorescence of NanoDRONEs parallels that known to be associated with the surface-bound FRET acceptor, which can be rapidly and significantly activated by ONOO$^-$, OCl$^-$, NO, *OH, and O$_2$*$^-$, but not by H$_2$O$_2$, NO$_2^-$, and NO$_3^-$. Importantly, NanoDRONEs exhibited an obvious fluorescence turn-on response to the most abundant reactive oxygen and nitrogen radicals in the regulation and progression of inflammation (ONOO, NO and O$_2$*$^-$) at pathophysiologically relevant concentrations (0.1 µM). However, under normal physiological conditions absent of inflammatory levels of RONS, the fluorescence of NanoDRONEs remained approximately the same after incubation for 24 h as shown in FIG. 8. Additionally, the NanoDRONEs of the disclosure showed decreased responses towards the same concentration of RONS (0.6 µM) in FBS-containing PBS due to the antioxidant complement present in FBS that can scavenge RONS and limit contact with NanoDRONEs. Therefore, the combination of high stability under normal physiological conditions and high, rapid fluorescence turn-on under pathophysiological conditions of inflammation suggests a critical balance of stability and sensitivity of the NanoDRONE for in vitro and in vivo inflammation imaging.

Figure 2C:
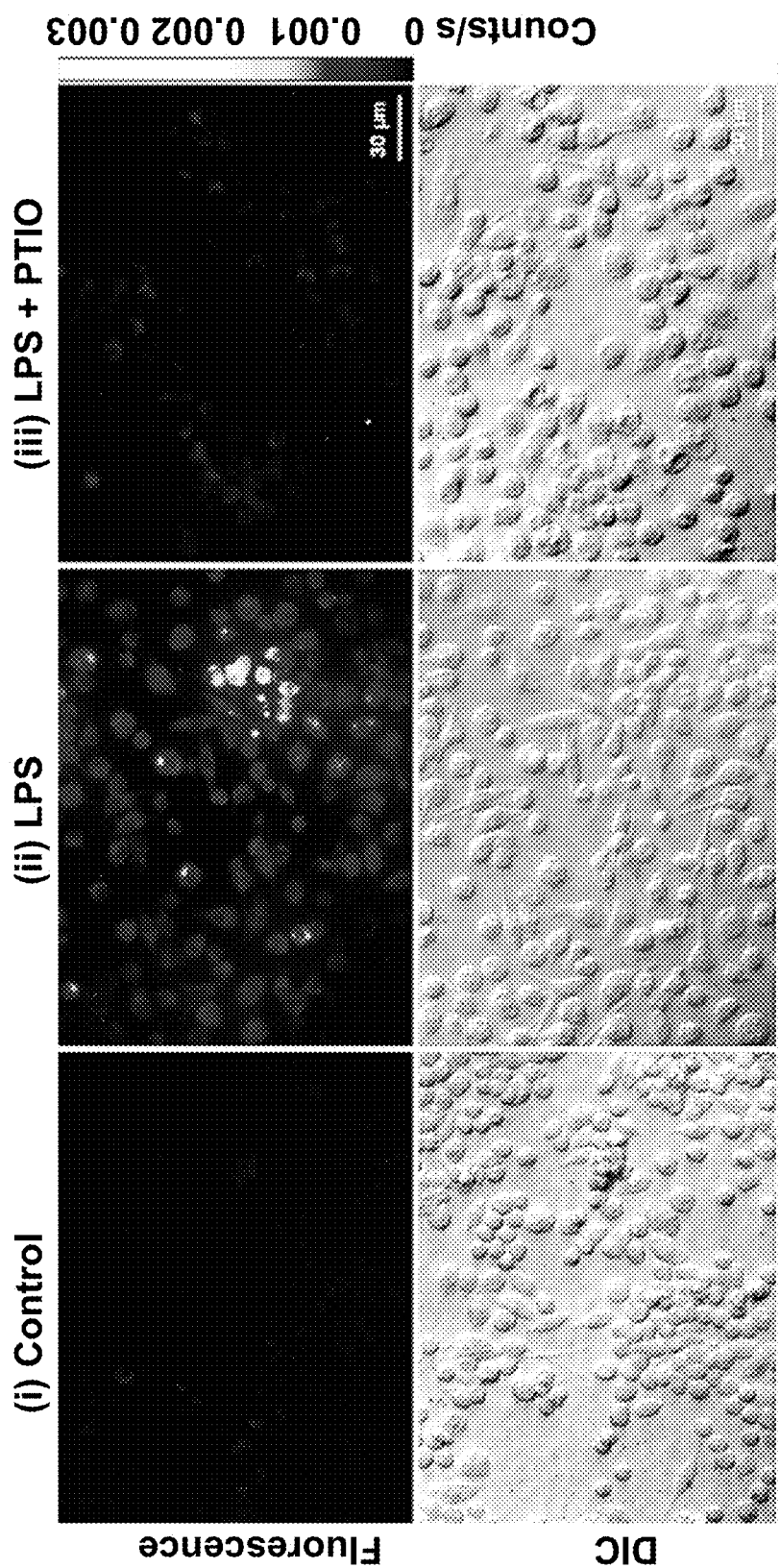

Response of NanoDRONEs to Stimulated Inflammatory Cells In Vitro:

The ability of NanoDRONEs to detect RONS in cultured cell types relevant to inflammation was examined. RAW 264.7, a murine macrophage cell line, showed very weak fluorescence after incubation with NanoDRONE in their resting state (FIG. 2C). To mimic the inflammatory condition that activates resting tissue macrophages, RAW 264.7 cells were pre-treated with bacterial cell wall lipopolysaccharide (LPS), a pathogen-associated molecular pattern (PAMP) known to activate macrophages to produce ONOO, NO, and O$_2^-$. With LPS pre-treatment, strong fluorescence was observed upon incubation with NanoDRONE, indicating the activation of the nanoprobe under conditions relevant to inflammation.

When the NO scavenger, 2-(4-carboxyphenyl)-4,4,5,5,-tetramethyl-imidazoline-1-oxyl-3-oxide (PTIO) was used to treat the cells along with LPS, followed by incubation with NanoDRONEs, no detectable fluorescence was clearly observed (FIG. 2C, (iii)), which confirmed RONS-mediated activation of NanoDRONEs.

Figure 9:
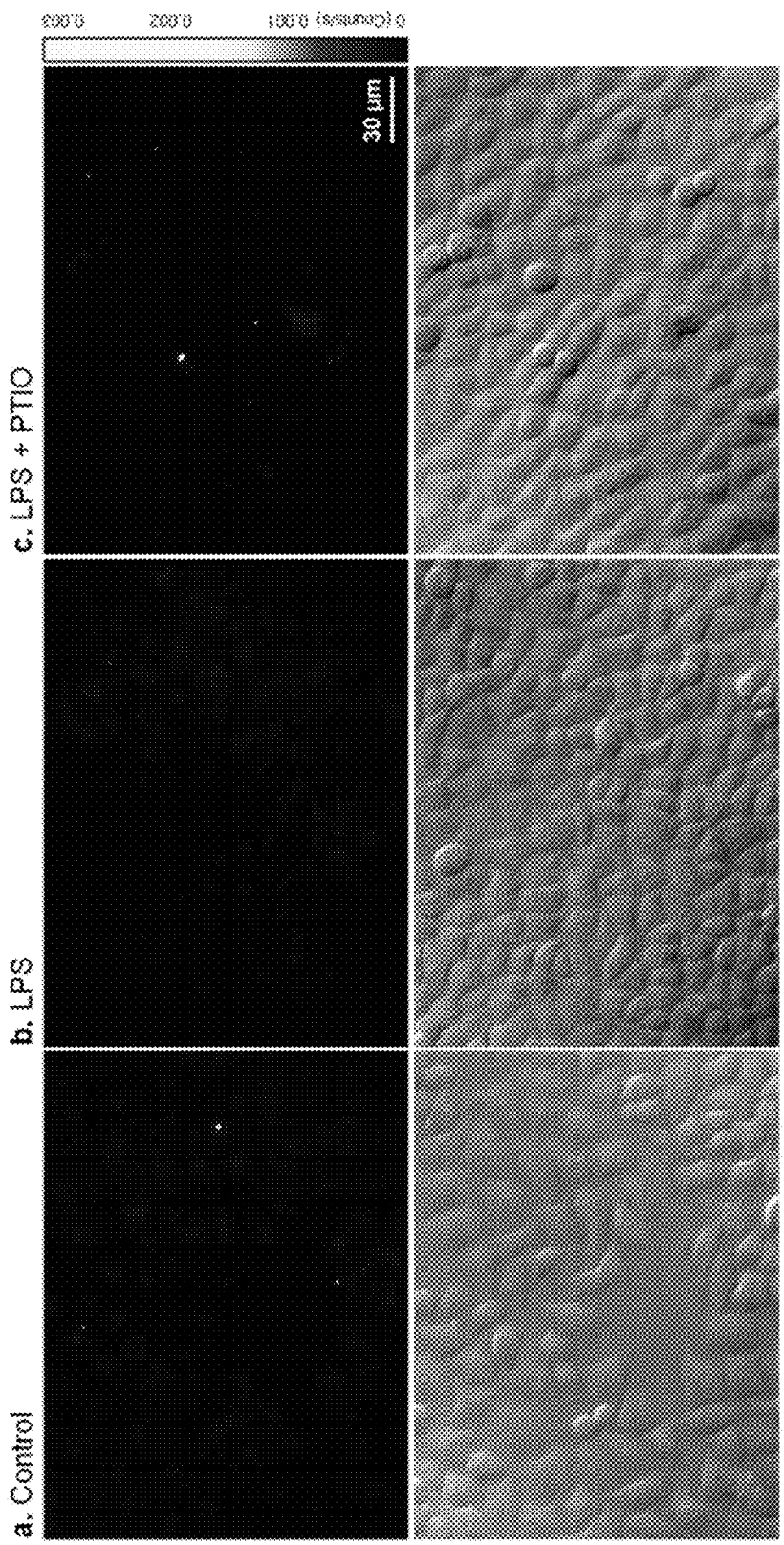
FIG. 9 is a series of digital fluorescence (top row) and DIC images (bottom row) of living HeLa cells. Panels (a): Cells incubated with NanoDRONE for 3 h; Panels (b): Cells pretreated with LPS for 12 h and then incubated with NanoDRONE for 3 h; Panels (c): Cells pretreated with LPS for 10 h, then with PTIO for 2 h, and further incubated with NanoDRONE for 3 h. NanoDRONE concentration=1.5 μg/mL; [LPS]=1 μg/mL; PTIO concentration=1 μg/mL.
Figure 10:
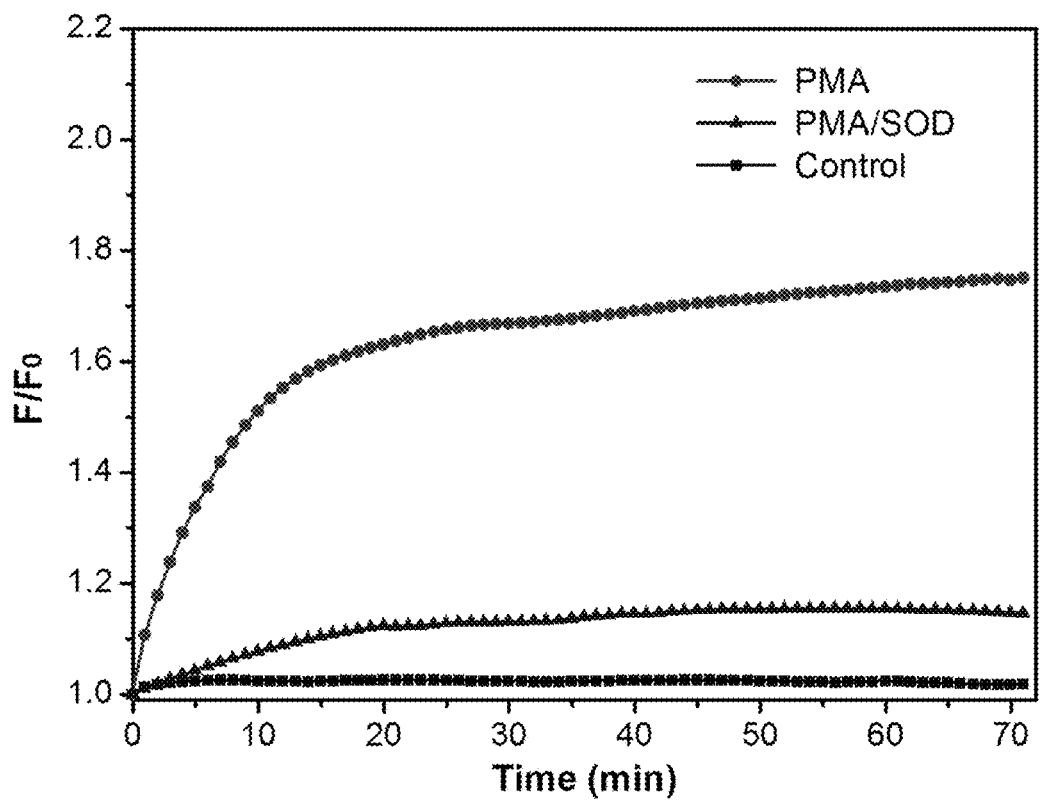
FIG. 10 is a graph illustrating the in vitro detection of endogenous $O_2^-$. Time-course of fluorescence changes of NanoDRONEs in the suspension of DMSO-differentiated HL60 cells pretreated with PMA or PMA/SOD. F and $F_0$ are the PL intensities, at $\lambda_{em}$=678 nm, at t and 0 min, respectively. NanoDRONE concentration=0.1 μg/mL based on CP; HL60 concentration=1×10^6 cells/mL; PMA concentration=1.5 μg/mL; SOD concentration=90 mU/mL.
Figure 11:
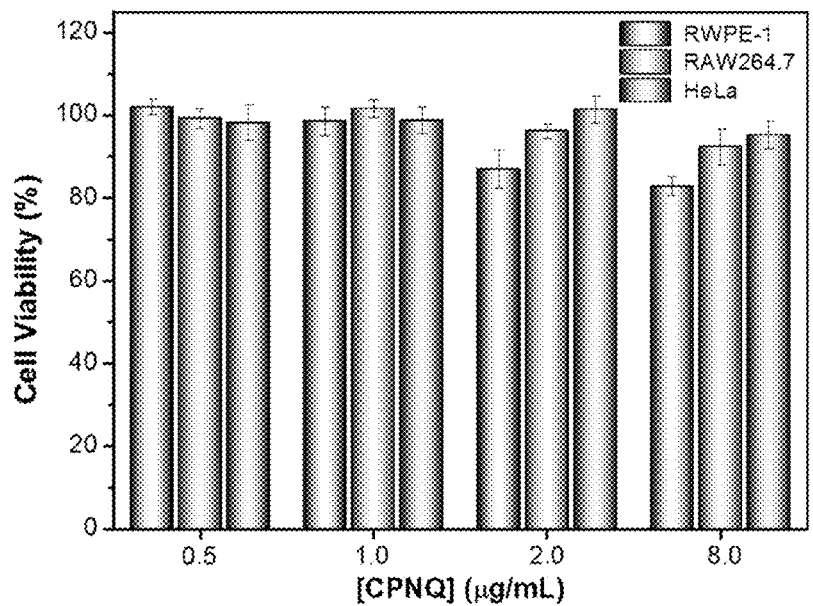
FIG. 11 is a graph illustrating the results of cytotoxicity studies of NanoDRONEs. In vitro viability of RWPE-1, RAW264.7 and HeLa cells treated with NanoDRONE solutions at 0.5, 1, 2, or 8 µg/mL for 24 h. The percentage cell viability of treated cells is calculated relative to that of untreated cells with a viability arbitrarily defined as 100%. Error bars are SD.

NanoDRONEs with DMSO-differentiated HL60 cells, which have a neutrophil phenotype, were also evaluated, as shown in FIG. 10. Upon stimulation of these neutrophil-like cells with phorbol myristate acetate (PMA), a known inducer of O$_2^-$, a significant NanoDRONE signal was observed over time, which was significantly suppressed by co-incubation of the cells with the O$_2^-$ scavenging enzyme superoxide dismutase (SOD). In control experiments, no turn-on fluorescence was observed for HeLa cells treated with LPS, as HeLa cells have no inflammatory response to LPS treatment (FIG. 9). These in vitro data demonstrate that NanoDRONEs can efficiently detect inflammation-associated RONS produced by cell mediators of the inflammatory process.

Figure 3A:
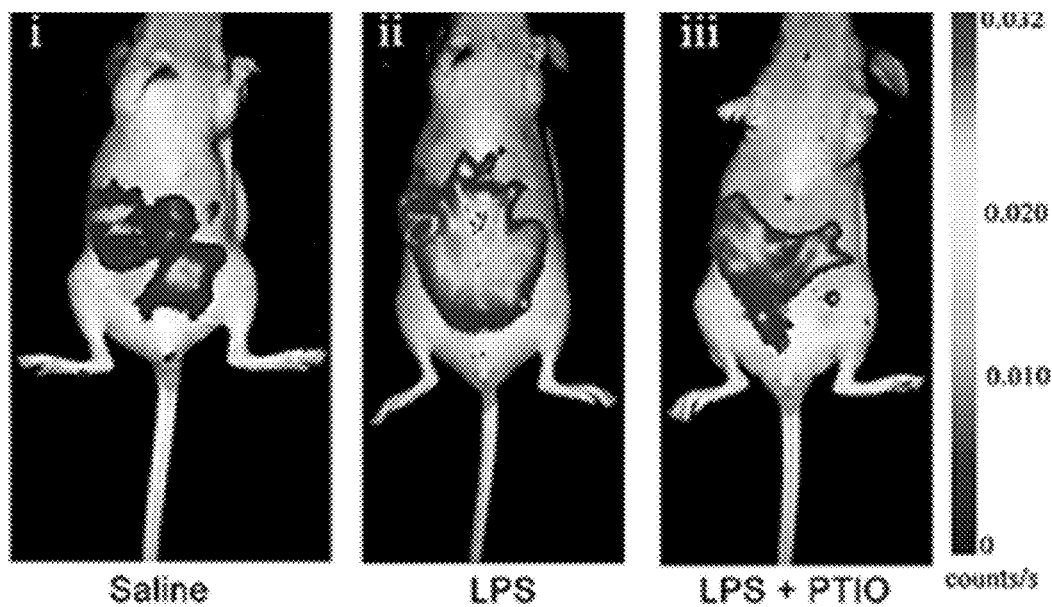
Figure 3B:
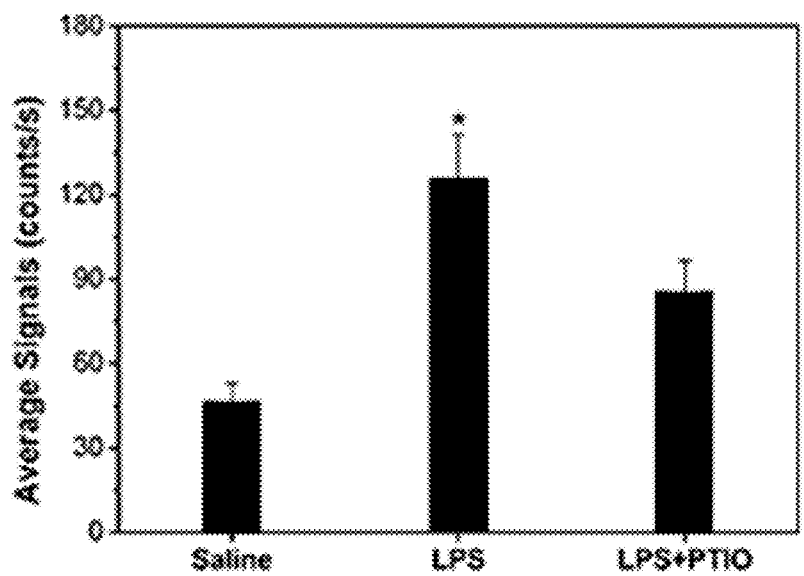
Figure 12A:
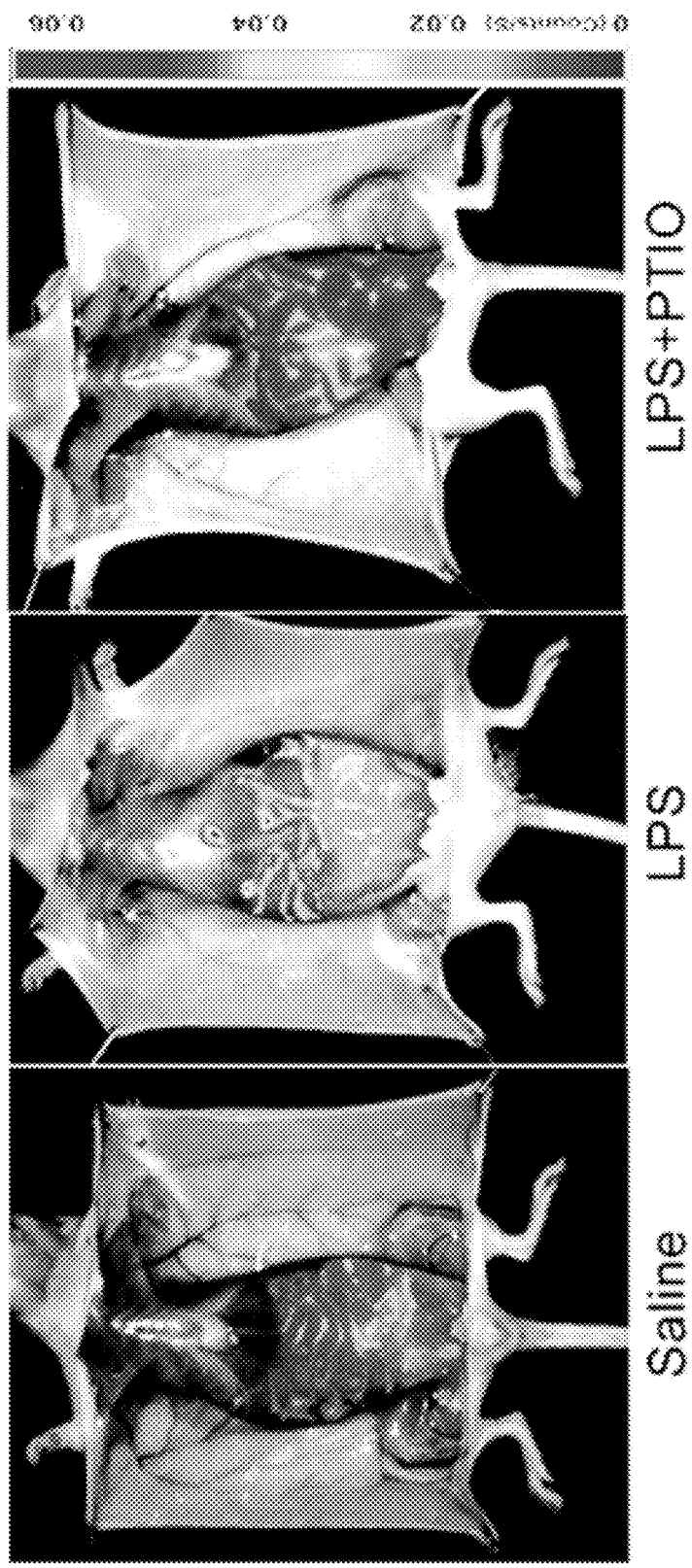
FIG. 12A is a series of digital images showing NanoDRONE activation evaluated in mouse models of LPS-induced peritonitis. LPS was administered intraperitoneally either alone or with the NO scavenger PTIO, followed 4 h later by i.p. administration of saline, NanoDRONEs, and NanoDRONEs with PTIO. Mice were euthanized 45 min after probe administration, and the skin was resected back to expose the intact peritoneal cavity, followed by fluorescence imaging.

In Vivo Detection of Inflammation after Local Administration: Peritonitis:

To directly follow up on the cell culture models employed, an animal model of peritonitis was induced by intraperitoneal (i.p.) injection of LPS, which has been used previously in the evaluation of other RONS-sensitive probes. Four hours after the injection of saline or LPS (FIG. 3A), NanoDRONEs were administered i.p., and a greater than three-fold activation of the nanoprobe occurred in the LPS-treated animals (FIG. 3B). To mechanistically involve the peritonitis-derived RONS in the activation of NanoDRONE, animals were treated with the NO scavenger PTIO i.p. (FIG. 3A, Panel (iii)). With the antioxidant activity of PTIO, there was a statistically significant decrease in NanoDRONE turn-on signal (FIG. 3B). In addition, exposure of the peritoneal cavity during necropsy confirmed the isolation of the observed fluorescence to the peritoneum and not the overlying skin (FIG. 12A).

Figure 12B:
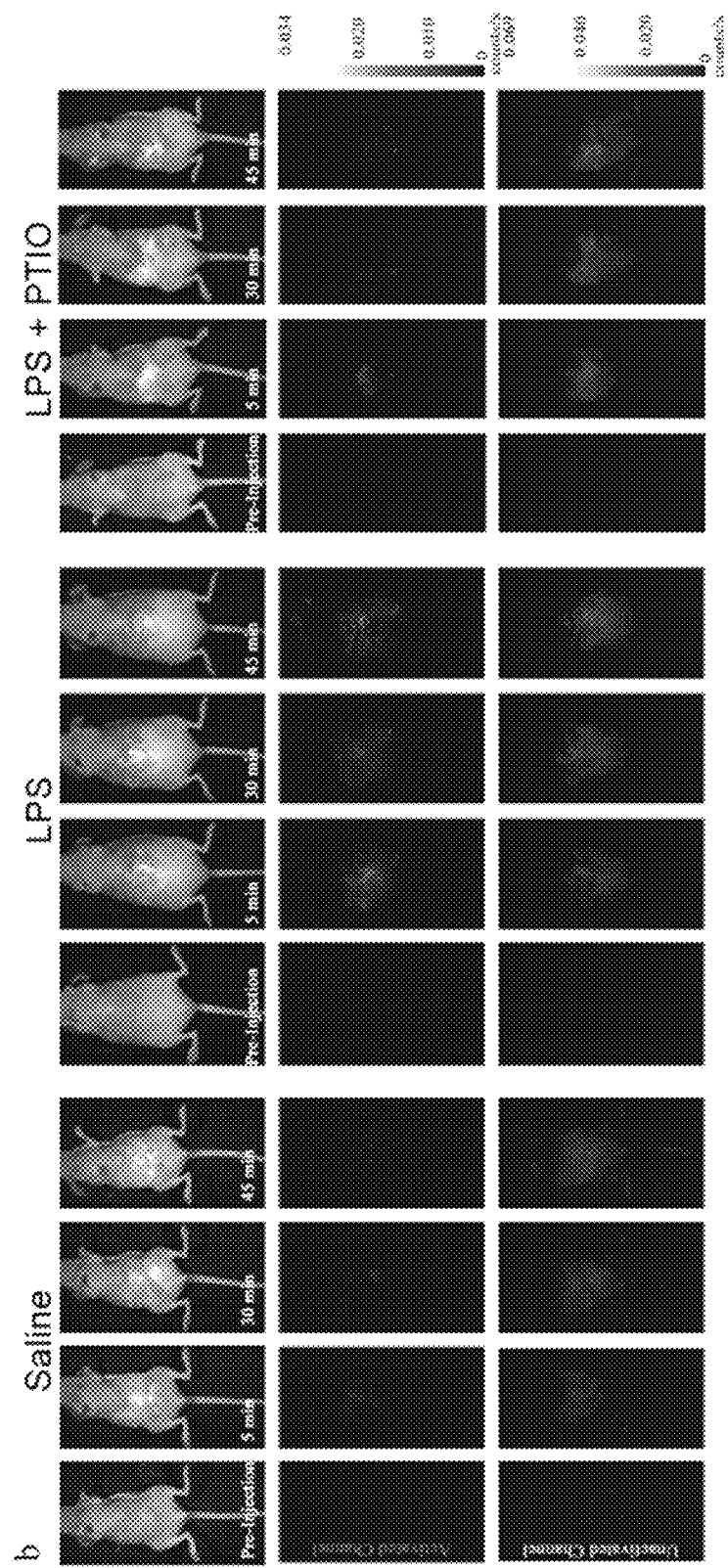
FIG. 12B is a series of digital images where mice were treated as described for FIG. 12A, and the images were deconvolved into activated NanoDRONE (dark) and non-activated NanoDRONE (light) spectra. The images depicted are (top row) overlaid with bright field image, (middle row) the activated channel alone, and (bottom row) the non-activated channel alone.
Figure 13A:
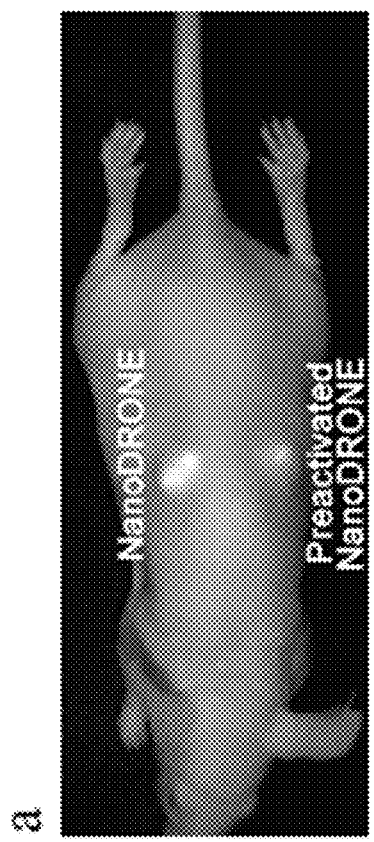
FIG. 13A is a digital image showing non-activated and preactivated NanoDRONEs injected subcutaneously into the back of a nude mouse followed by fluorescence hyperspectral imaging to record the in vivo spectra of the activated and non-activated probes, and autofluorescence.
Figure 13B:
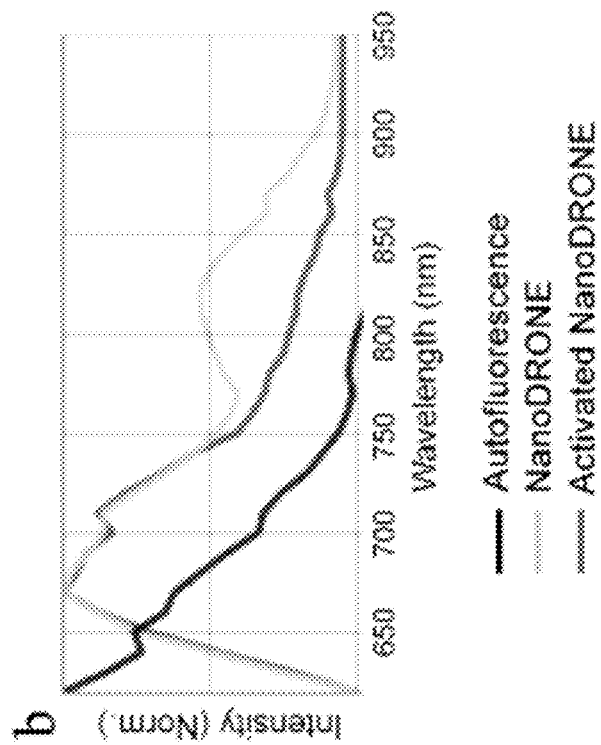
FIG. 13B is a graph illustrating the spectra used to deconvolve all acquired in vivo fluorescence imaging.

Since the NanoDRONEs of the disclosure had a spectral fingerprint dependent on their state of activation, hyperspectral in vivo fluorescence imaging was employed to deconvolve non-activated from activated probes (FIG. 13), which were differentiated in vivo by the surface fluorophore fluorescence at approximately 840 nm to permit simultaneous imaging of both states of the nanoprobe. Applying this hyperspectral deconvolution in vivo to the LPS peritonitis model confirmed the significantly enhanced turn-on of the nanoprobe in LPS-treated animals relative to saline and PTIO control groups (FIG. 12B).

Figure 14A:
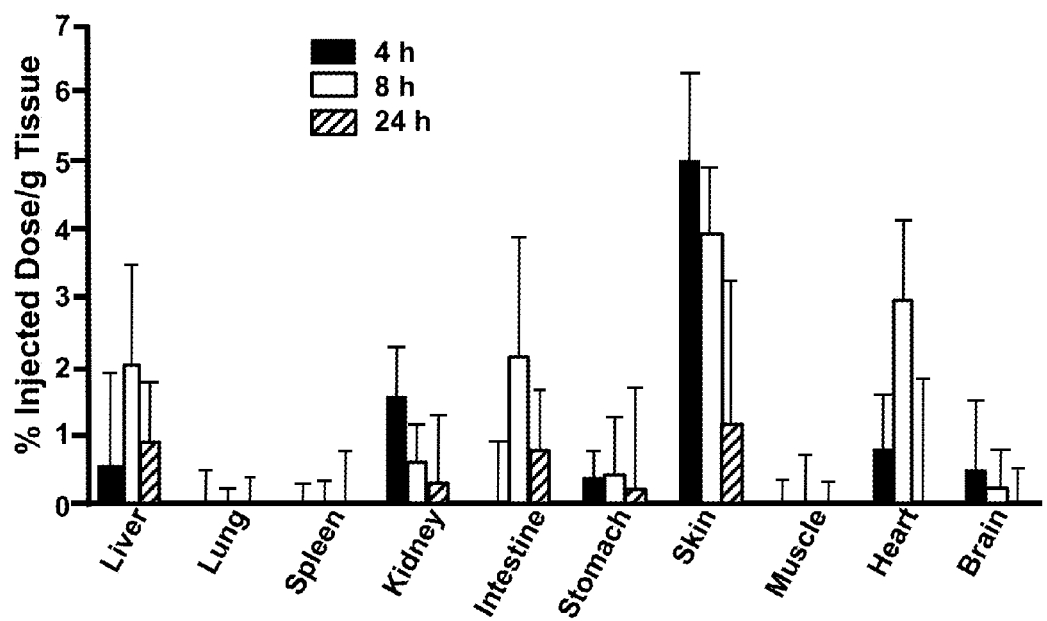
FIG. 14A is a graph illustrating the tissue distribution levels determined in healthy nude mice following the intravenous administration of 0.1 mg NanoDRONEs and homogenization of isolated tissues following animal euthanasia at the given time points of 4 h (left bar), 8 h (center bar), and 24 h (right bar). All values are corrected for tissue background without the administration of nanoparticles.
Figure 14B:
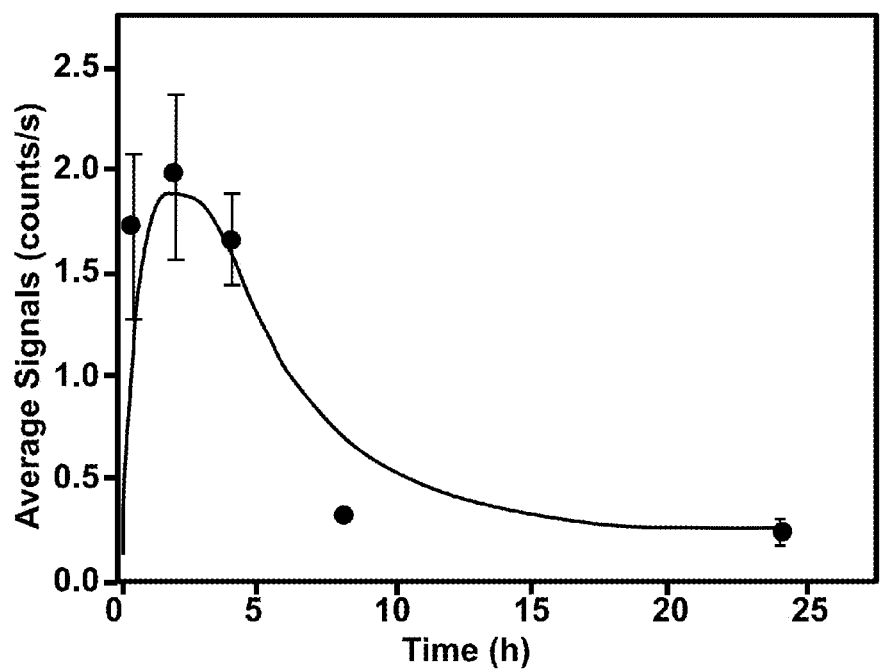
FIG. 14B is a graph illustrating the blood levels determined through serial saphenous vein sampling following the intravenous administration of probe, followed by the activation of all NanoDRONEs by the addition of the ONOO generator SIN-1.

Evaluation of NanoDRONEs for Systemic Administration:

The intravenous injection of NanoDRONEs (0.1 mg) into normal nude mice resulted in dynamic accumulation in the liver, kidney, gastrointestinal tract, skin, heart and brain, all of which decreased with time (FIG. 14A). Notably, organs of the reticuloendothelial system (RES) such as the liver and spleen, did not display higher nanoparticle uptake than non-reticuloendothelial tissues (e.g. skin, kidney, gastrointestinal tract, heart), suggesting enhanced biocompatibility and the ability of NanoDRONEs to evade RES uptake. The blood circulation time was measured through repeated saphenous vein sampling, indicating a circulation half-life of approximately 6 h (FIG. 14B). The relatively long circulation time and favorable biodistribution of NanoDRONEs, in conjunction with the lack of any overt systemic toxicity of the formulation, suggests that NanoDRONEs are amenable to systemic administration and capable of whole animal sensing for inflammatory microenvironments.

In Vivo Detection of Inflammation after Systemic Administration:

Spontaneous Bacterial Infection Model: Since inflammation can be induced by both pathogen-associated molecular pattern (PAMPs) and danger-associated molecular patterns (DAMPs) following bacterial infection and traumatic tissue injury, respectively, NanoDRONEs of the disclosure were evaluated following systemic administration in mouse models of spontaneous bacterial infection and ear hole punch-induced injury.

Nude mice are susceptible to skin infection by *Corynebacterium bovis* (*C. bovis*), which results in hyperkaratotic orthokeratosis and mononuclear cell infiltration, and inflammation localized to regions of infection. Accordingly, mice spontaneously infected by *C. bovis* were administered NanoDRONEs intravenously at the first sign of raised red skin lesions.

Figures 3C, 3D:
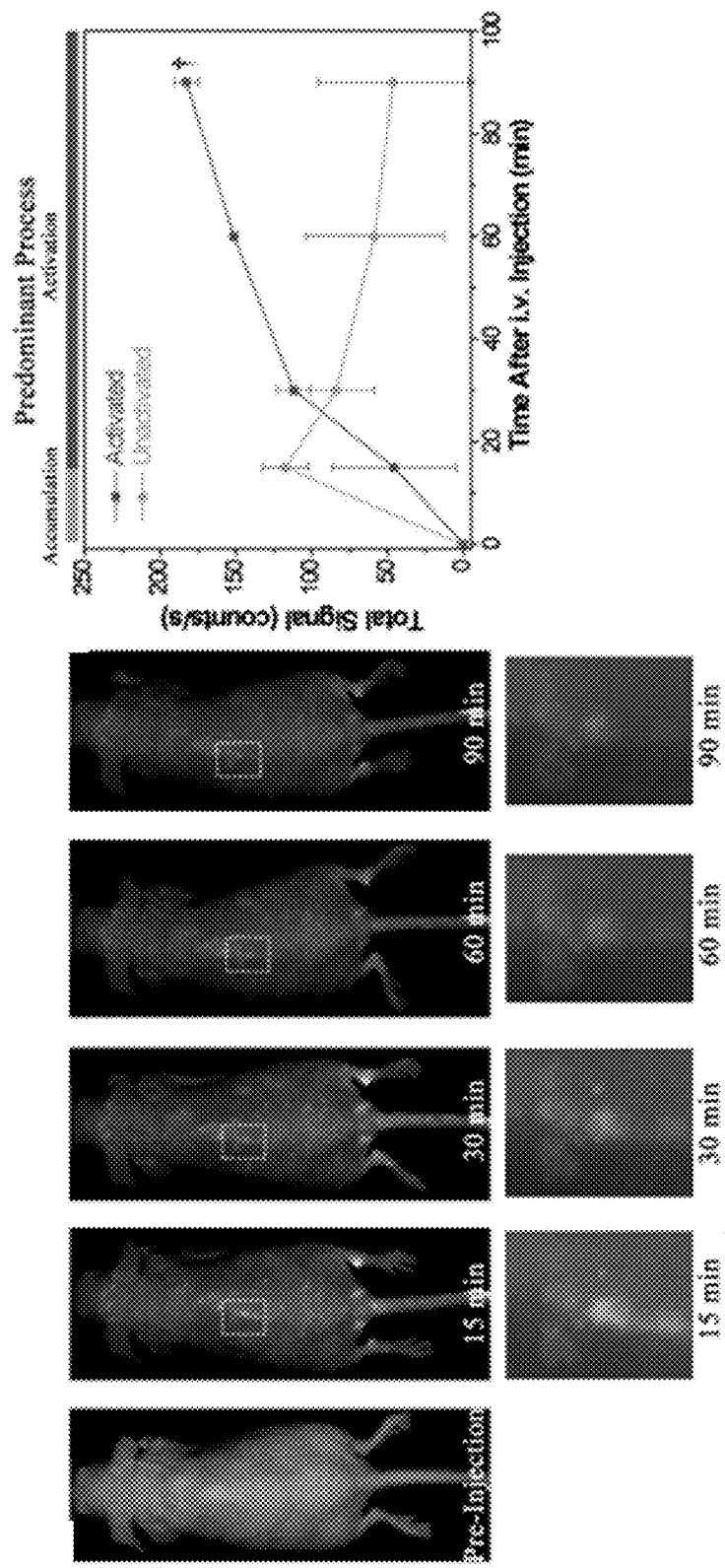
Figure 15A:
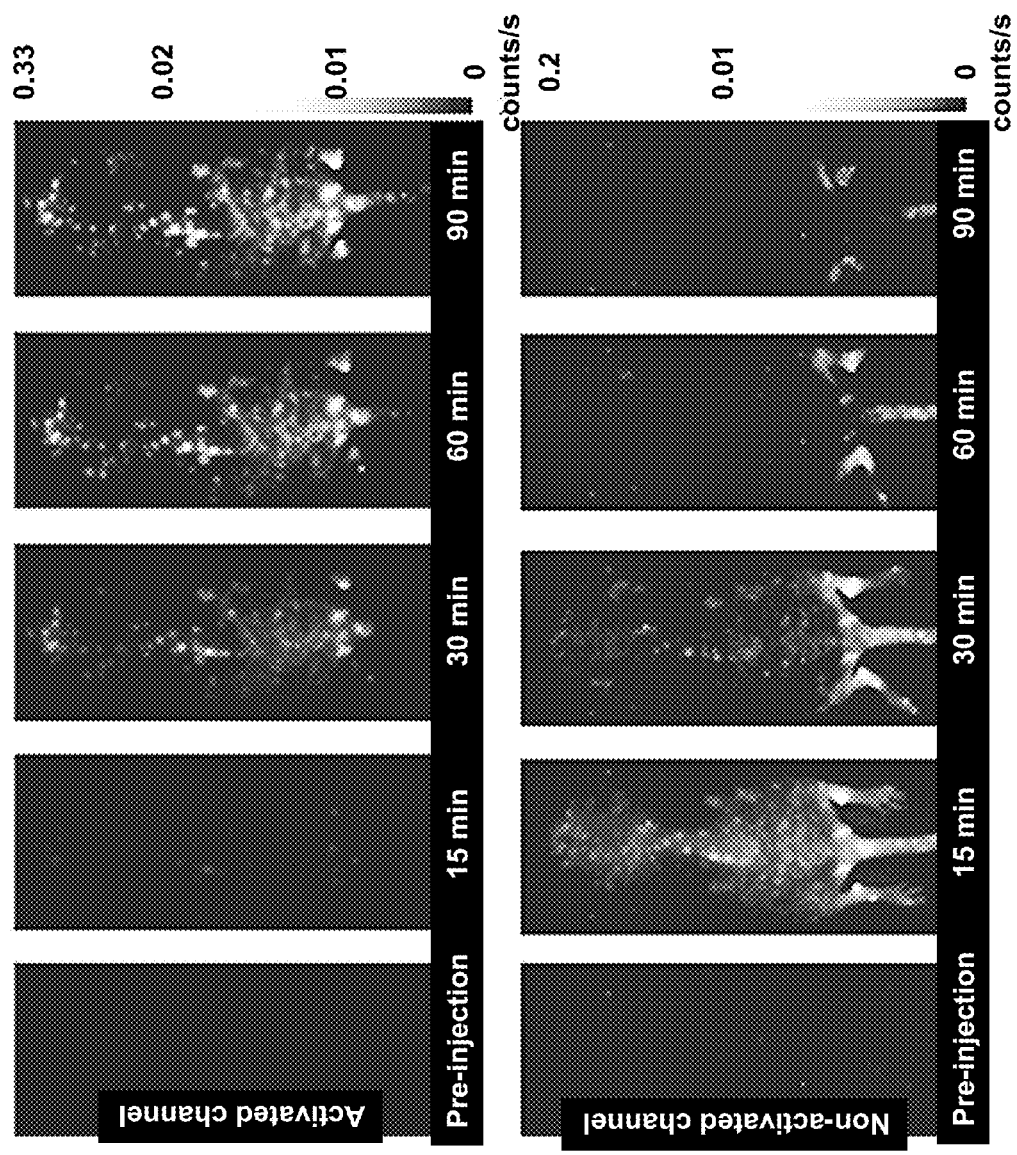
FIGS. 15A and 15B illustrate the evaluation of NanoDRONEs in a mouse model of spontaneous bacterial infection with *Corynebacterium bovis*.
Figure 15B:
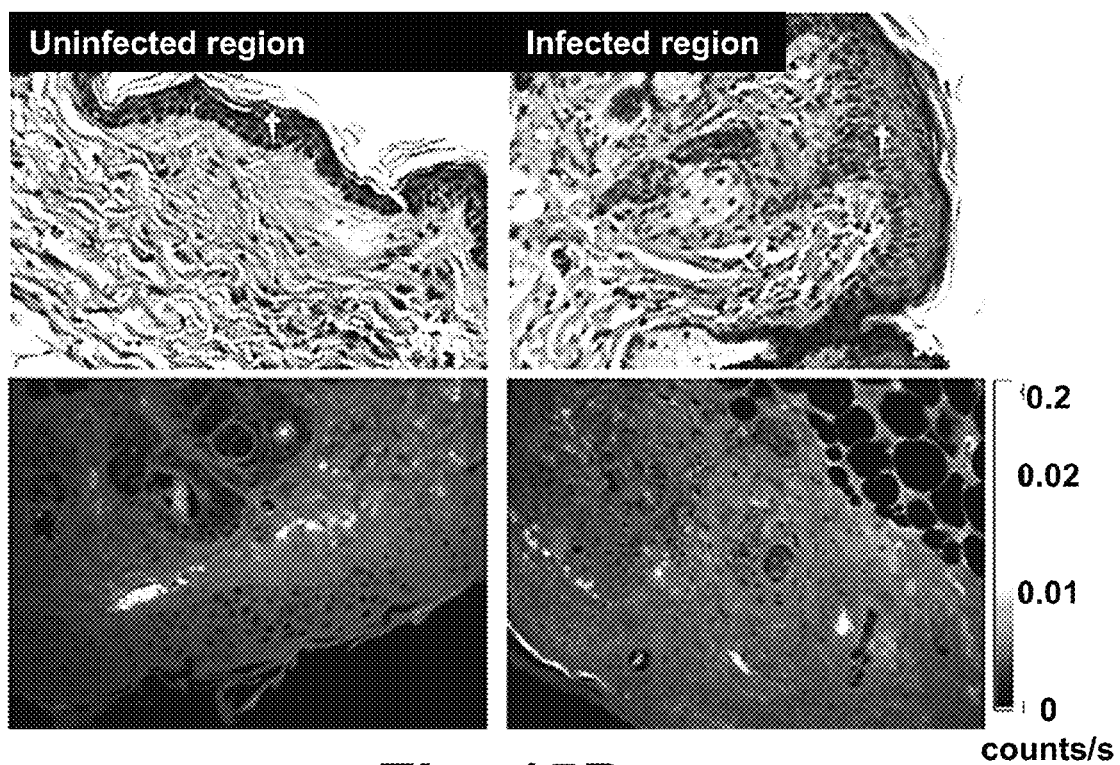

The NanoDRONEs were observed to accumulate in the infected foci of the skin and to be activated within 15 minutes of administration (FIG. 3C). As the inset figures demonstrate, there is a progressive change in NanoDRONEs from the non-activated to activated form. This change in predominant process from the initial accumulation of non-activated NanoDRONE at the site of bacterial inflammation to probe activation was revealed by hyperspectral in vivo fluorescence imaging (FIG. 15A), and quantified using the whole animal as region of interest (FIG. 3D). The two phases, accumulation and activation, were clearly displayed, with the time-dependent increase in activated NanoDRONE signal being statistically greater than the non-activated signal. In addition, the ability of NanoDRONEs to identify inflammatory microenvironments following systemic administration was confirmed by the differential distribution of probe between regions of *C. bovis* infected and uninfected skin. While the nanoprobe was confined to vasculature in histologically uninfected regions of skin (left image, FIG. 15B), regions of infected skin showed clear NanoDRONE extravasation and distribution throughout the tissue (right image, FIG. 15A).

In Vivo Detection of Inflammation after Systemic Administration (Sterile Tissue Injury Model):

To detect inflammatory microenvironments induced by sterile injury-initiated DAMP signaling, NanoDRONEs were administered to nude mice intravenously, and 4 h later, a 2 mm hole was made in the distal pina of the ear. Prior to the induction of injury, low levels of fluorescence from the non-activated probe were observed in the mouse ear (FIG. 3E), which increased in intensity within 5 minutes after injury, demonstrating the rapid accumulation of NanoDRONE in inflammatory microenvironments. By 10 minutes after injury, significant activation of NanoDRONEs was observed circumferentially to the injury site, which increased in intensity over time (FIG. 3E).

Figure 16:
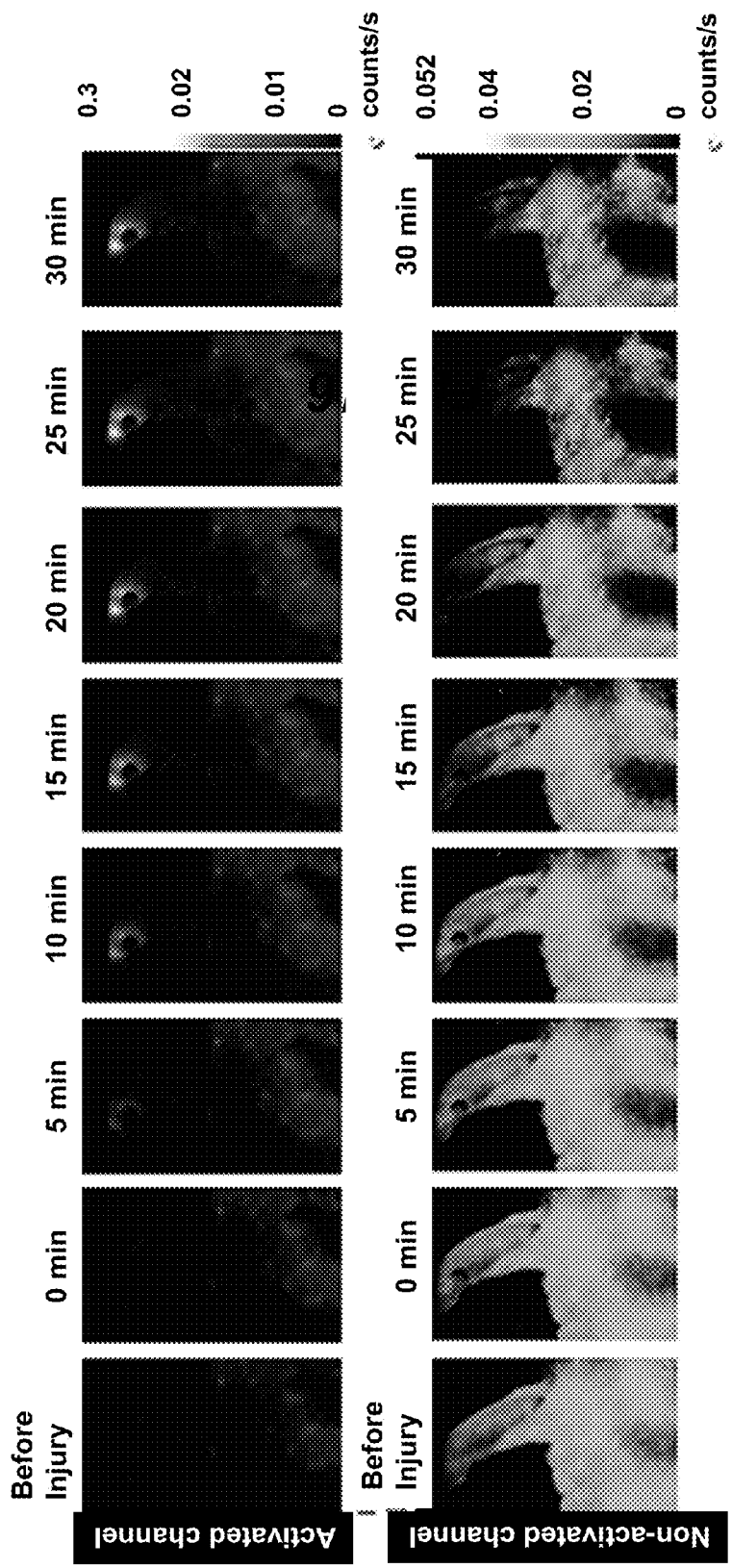
FIG. 16 is a series of digital images for the evaluation of NanoDRONEs in a mouse model of sterile tissue injury. Nanoparticles were administered intravenously 4 h before the induction of tissue trauma into the distal ear pina. Fluorescence hyperspectral imaging was performed over time for the real-time monitoring of the progression of inflammation. For the purpose of quantitation, the fluorescence from activated (top) and non-activated (bottom) NanoDRONEs were deconvolved following hyperspectral imaging.

Hyperspectral in vivo fluorescence imaging was performed (FIG. 16) and the intensity of the activated and non-activated channels was quantified with the entire ear as the region of interest (FIG. 3F). The procession of the NanoDRONEs from an accumulation phase to activation phase in the detection of inflammatory microenvironments observed in the bacterial infection model was recapitulated in the sterile injury model.

Since inflammation is a dynamic process that proceeds from early (transcription independent) to late (transcription dependent) phases, culminating in the restitution of injury, the ability of NanoDRONE to detect both the late inflammatory and restitution phases was also assessed (FIG. 3G). Ear hole punches were made in the distal pina of mice and left to heal for 24 hours or 14 days, representing late inflammation and restitution phases, respectively, following which time nanoparticles were administered intravenously. Late-stage inflammation was successfully detected circumferential to the ear hole 24 hours after induction (FIG. 3G, right ear). However, no fluorescent signal was observed in the ear after restitution (FIG. 3G, left ear). Therefore, NanoDRONEs can detect both early- and late-phase inflammatory microenvironments, but are not activated once restitution has occurred and inflammation has ceased.

Figure 4A:
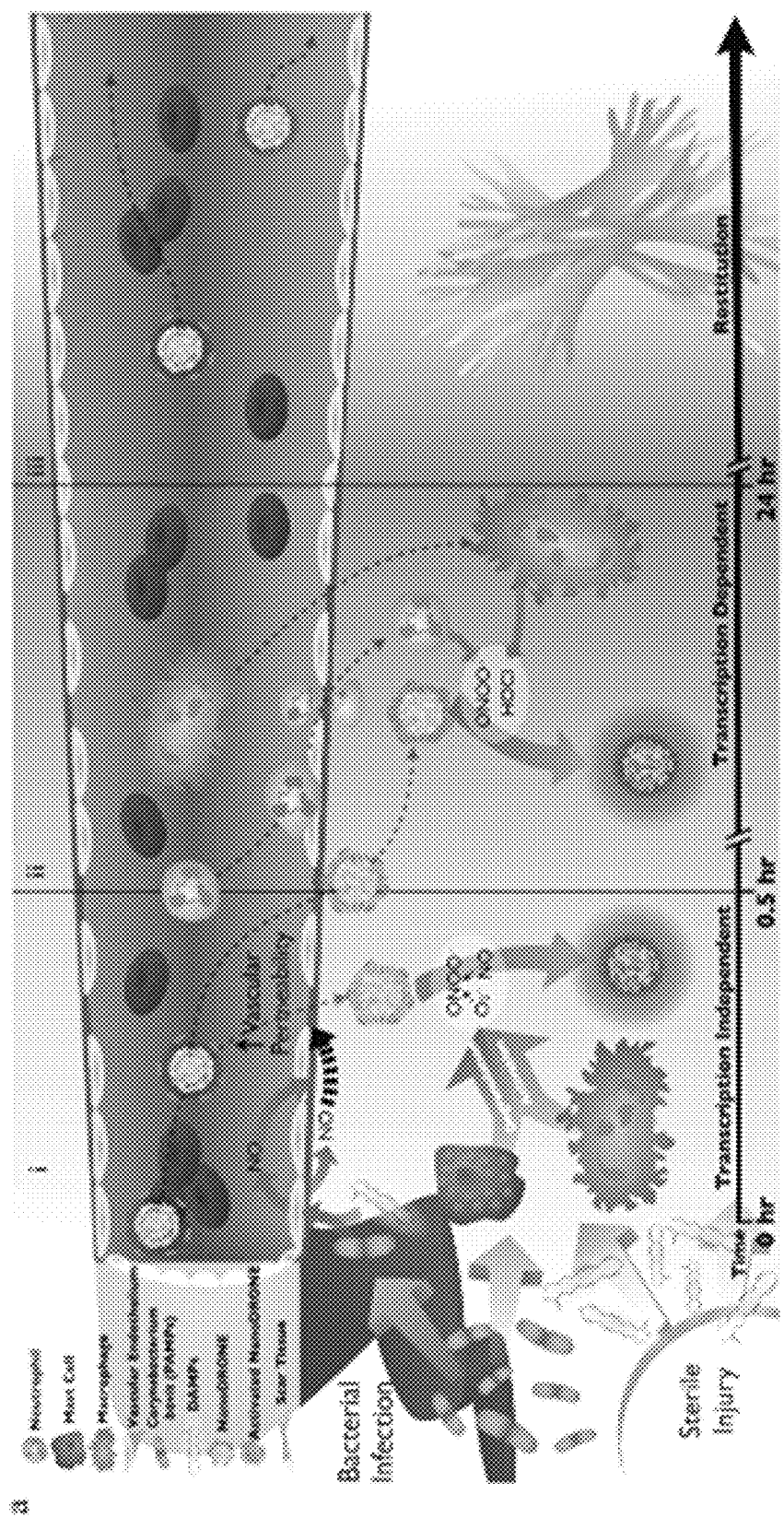
FIGS. 4A and 4B illustrate that NanoDRONEs are capable of indicating the RONS concentration changes in tissue microenvironments during both early and late inflammation, but remain non-activated in the regions of previous inflammation following restitution.

Mechanism of In Vivo Detection of Inflammation:

The detection of inflammation by NanoDRONEs can be reconciled with the physiological and chemical microenvironmental changes following infection or injury (FIG. 4A). Upon bacterial infection or sterile injury, PAMPs and DAMPs, respectively, are released from the injured cells to stimulate the local tissue mast cells and macrophages to release RONS through respective degranulation or activation mechanisms. This chemical change in the local injury microenvironment initiates the early, transcription-independent phase of inflammation, during which time vascular endothelial cells are induced directly by PAMP/DAMP signaling, or by mast cell/macrophage-derived RONS to produce NO (FIG. 4A).

Figure 4B:
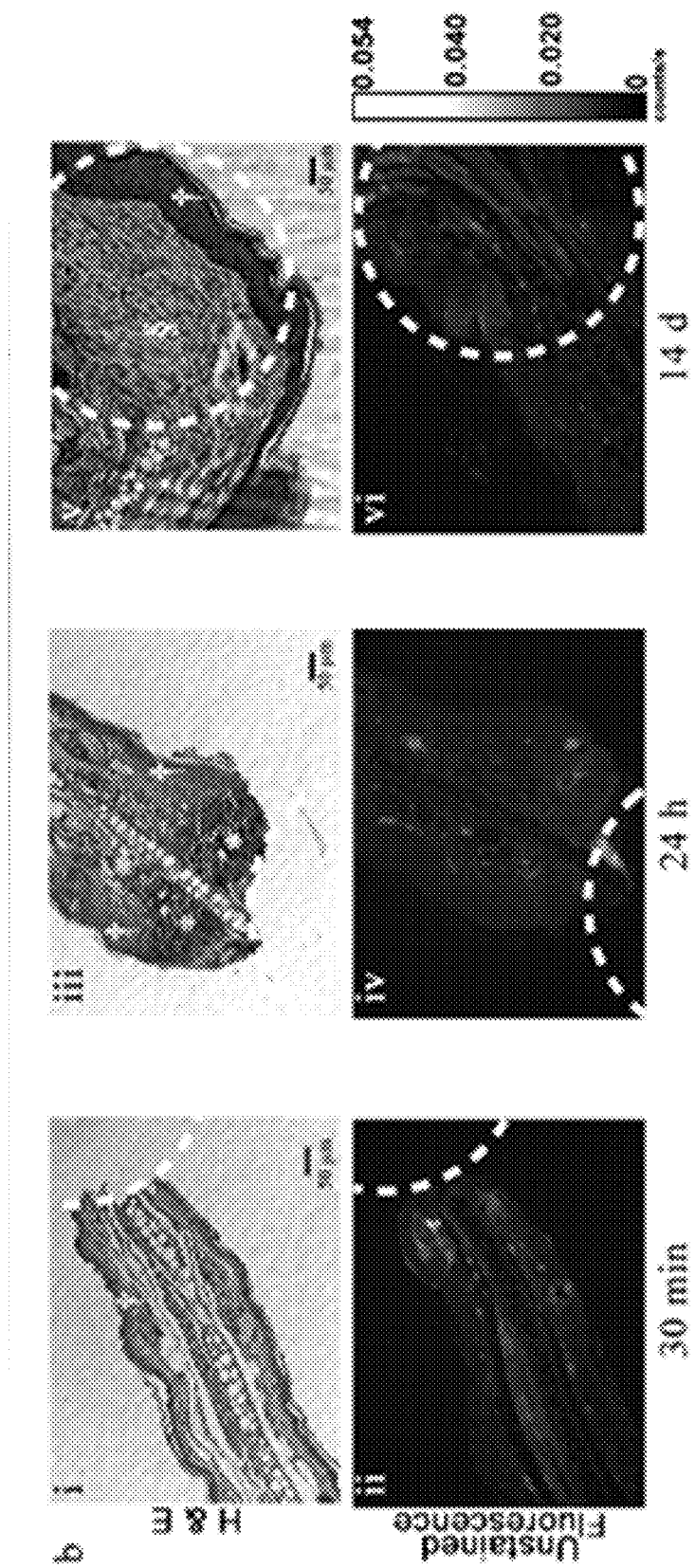

The release of NO from vascular endothelium enhances vascular permeability to the injured tissue, and at the same time intracellular NO initiates a transcription process that ultimately changes the local vascular lumen and recruits neutrophils and additional macrophages to the site of injury. Within the early stage of inflammation, the enhanced vascular permeability permits the rapid accumulation of NanoDRONEs at inflammatory sites, followed by in-situ activation and luminescence of NanoDRONEs by high local RONS concentrations. Within 30 mins of sterile injury, prior to the arrival of any cellular mediators of inflammation (FIG. 4B, i), this local accumulation and activation of NanoDRONEs in the inflammatory microenvironment was revealed histologically (FIG. 4B, ii). With the progression of inflammation from the early to the late (transcription-dependent) phase over time (FIG. 4B, ii), the arrival of neutrophils and macrophages to the site of injury, assisted by the maintenance of enhanced local vascular permeability, further increases microenvironmental RONS concentrations.

The infiltration of injured tissue by inflammatory cells 24 hours following injury (FIG. 4B, iii) was accompanied by a more wide-spread accumulation and activation of NanoDRONEs in the injured tissue (FIG. 4B, iv), as revealed by histological analysis. With the cessation of inflammatory stimuli following restitution of the injury and formation of scar tissue (FIG. 4B, iii), vascular permeability decreases and local tissue RONS concentrations return to physiological basal levels. With the confirmation of restitution by the appearance of fibrotic scar tissue within the site of tissue injury (FIG. 4B, v), NanoDRONEs were only observed within the vasculature of the tissue (FIG. 4B, vi), rationalizing the absence of activated fluorescence after wound healing in vivo (FIG. 3G). The in vivo data obtained from all three animal models of inflammation confirms that NanoDRONEs sense inflammation independent of its cause and type, but rather respond to the chemical changes in the immediate inflammatory microenvironment that occur early in infection or injury and remain late into the inflammatory process.

The nanoparticles of the disclosure, herein termed "NanoDRONEs" are fluorescent probe capable of systemic monitoring of inflammatory microenvironments through sensing elevated levels of RONS that are key chemical mediators of the inflammatory cascade. This capability derives from the nanoarchitecture of the probe design, meeting criteria considered essential for in vivo imaging, including, but not limited to, factors such as biocompatibility, physiological stability, good biodistribution and circulation half-life, and rapid targeting of leaky inflammatory microvasculature. The RONS-sensitive fluorophore molecules as energy-accepting surface antennae to collectively yield dual-color fluorescent signals allow hyperspectral in vivo fluorescence imaging of RONS during inflammation associated with injury and disease.

The rapid accumulation of NanoDRONEs at inflammation sites, due to the leaky inflammatory vasculature, and their sensitive responses to the most highly reactive RONS, particularly $ONOO^-$ and NO, allow them to undergo nearly immediate activation in inflammatory microenvironments. Therefore, NanoDRONE nanoprobes not only provide the advantage of increased output response in real time at lower dosing levels over existing fluorescent probes, but also make the imaging of early stage inflammation feasible. In addition, due to the instant change in the spectral fingerprint of NanoDRONE in response to RONS, its activation status can be qualitatively imaged to correlate with the extent of inflammation, and provide more robust detection of pathophysiology.

The sensitivity of NanoDRONE to the chemical changes in the inflammatory microenvironment also provides key advantages over other mechanisms for the detection of inflammation (e.g. cell tracking), which are (i) the ability to detect inflammation independent of the cellular composition of tissues, and (ii) the ability to detect inflammation nearly at the time of initiation, much earlier than methods reliant upon the migration of leukocytes, neutrophils, or macrophages. With the ultimate goal of molecular imaging being for the management of disease through improved diagnostics and enhanced therapy, it follows that inflammation should be detected at subclinical stages to achieve the best therapeutic results. Subclinical indications of inflammation manifest only histologically and precede any visible signs of pathophysiology. Thus, the ability of NanoDRONEs to respond to elevations in RONS that are characteristic of inflammation precede even these subclinical histological changes, permitting the earliest possible detection of inflammation.

Accordingly, the novel nanoparticle-based dual-color molecular imaging probes of the disclosure represent a significant innovation in the molecular imaging of inflammation. NanoDRONEs provide systemic administration and a temporal resolution unattainable by any other diagnostic methods. In addition to whole body monitoring of bacterial infection and tissue trauma as demonstrated herein, NanoDRONEs have the potential to provide real-time, in situ information regarding the inflammatory status of many disease states. With the modularity of the design, the sensing capability of NanoDRONEs may extend beyond RONS. The simple conjugation of fluorophores sensitive to any given chemical species, be it RONS, reductive species, or alkylating species, to the surface of the nanoparticle will specify the environmental sensing capacity of the nanoprobe. With the maintenance of the core components of the probe that make the nanoparticle a stable, biocompatible fluorescent molecular imaging probe, NanoDRONEs can serve as a probe platform for systemic, in situ and real-time imaging of chemical changes in the microenvironment of pathological processes.

One aspect of the disclosure, therefore, encompasses embodiments of a composition comprising a nanoparticle probe, wherein said nanoparticle probe can comprise: a nanoparticle core comprising a detectable signal emitter; and a quencher moiety, wherein the ability of the quencher to quench a signal from the emitter is substantially reduced on contact of the nanoparticle probe with a reactive oxygen and nitrogen species (RONS).

In embodiments of this aspect of the disclosure, the nanoparticle core can have a shell substantially surrounding the said nanoparticle core, wherein the shell can have the quencher linked thereto.

In embodiments of this aspect of the disclosure, the quencher can be linked to the detectable signal emitter by a linker cleavable by a reactive oxygen and nitrogen species (RONS).

In embodiments of this aspect of the disclosure, the quencher can be degradable by a reactive oxygen and nitrogen species (RONS).

In embodiments of this aspect of the disclosure, the nanoparticle core can comprise a superconducting polymer.

In these embodiments of this aspect of the disclosure, the superconducting polymer can be selected from the group consisting of: Poly[2-methoxy-5-(2-ethylhexyl-oxy)-1,4-phenylene-vinylene], Poly[2-methoxy-5-(2-ethylhexyloxy)-1,4-(1-cyanovinylene-1,4-phenylene)]; Poly[(9,9-dioctyl-2,7-divinylenefluorenylene)-alt-co-(9,10-anthracene)], Poly[{9,9-dihexyl-2,7-bis(1-cyanovinylene)fluorenylene}-alt-co-{2,5-bis(N,N'-diphenylamino)-1,4-phenylene}], Poly[(9,9-dioctylfluorenyl-2,7-diyl)-alt-(benzo[2,1,3]thiadiazol-4,7-diyl)], Poly[2,7-(9,9-di-octyl-fluorene)-alt-4,7-bis(thiophen-2-yl)benzo-2,1,3-thiadiazole], Poly[2,6-(4,4'-bis(2-ethylhexyl)dithieno[3,2-b:2',3'-d]silole)-alt-4,7(2,1,3-benzothiadiazole)], Poly[2,7-(9,9-di-octyl-fluorene)-alt-4,7- bis(thiophen-2-yl)benzo-2,1,3-thiadiazole], Poly[N-9'-heptadecanyl-2,7-carbazole-alt-5,5-(4',7'-di-2-thienyl-2',1',3'-benzothiadiazole)], Poly[3-hexylthiophene-2,5-diyl], and Poly[2,5-bis(3-dodecylthiophen-2-yl)thieno[3,2-b]thiophene].

In embodiments of this aspect of the disclosure, the detectable signal emitter can be a fluorophore and the signal emitted therefrom is quenched by FRET to the quencher.

In embodiments of this aspect of the disclosure, the nanoparticle probe can be an $NH_2$-functionalized conjugated polymer nanoparticle ($NH_2$-CPN) comprising a core nanoparticle comprising: poly[9,9'-dihexyl-2,7-bis(1-cyanovinylene)fluorenylene-alt-co-2,5-bis(N,N'-diphenylamino)-1,4-phenylene] (PCFDP) and the hydrophobic lipid tails of 1,2-Dimyristoyl-sn-glycero-3-phosphoethanolamine-N-[methoxy(polyethylene glycol)-2000] (DSPE-PEG) and 1,2-distearoyl-sn-glycero-3-phosphoethanolamine-N-[amino(polyethylene glycol)-2000] (DSPE-PEG-$NH_2$), whereby the N-[methoxy(polyethylene glycol)-2000] domain of the DSPE-PEG, and the N-[amino(polyethylene glycol)-2000] domain of the DSPE-PEG-$NH_2$ comprise the shell substantially surrounding the core nanoparticle; and the dye (IR-775-COOH) conjugated to the shell.

In embodiments of this aspect of the disclosure, the composition can further comprise a pharmaceutically acceptable carrier.

Another aspect of the disclosure encompasses embodiments of a method of detecting a site of inflammation in a human or non-human animal subject, the method comprising the steps of: (a) administering to a human or non-human subject a pharmaceutically acceptable composition comprising a population of nanoparticle probes wherein said nanoparticle probes can each comprise: a nanoparticle core comprising a detectable signal emitter; and a quencher moiety, wherein the ability of the quencher to quench a signal from the emitter is substantially reduced on contact of the nanoparticle probe with a reactive oxygen and nitrogen species (RONS); (b) allowing the nanoparticle probes of the administered pharmaceutically acceptable composition to contact a site of inflammation in the subject animal or human; (c) generating a detectable signal from the detectable signal emitter; (d) detecting the signal emitted from the detectable signal emitter; and (e) locating the position of the detectable signal relative to the anatomy of the human or non-human animal subject, thereby identifying a site of inflammation in the human or non-human animal subject.

In embodiments of this aspect of the disclosure, the pharmaceutically acceptable composition can be administered to the human or non-human animal subject topically, intravenously, intraperitoneally, or by injection to a site suspected of being inflamed.

In embodiments of this aspect of the disclosure, the nanoparticle core can have a shell substantially surrounding the said nanoparticle core, wherein the shell can have the quencher linked thereto.

In embodiments of this aspect of the disclosure, the quencher can be linked to the detectable signal emitter by a linker cleavable by a reactive oxygen and nitrogen species (RONS).

In embodiments of this aspect of the disclosure, the quencher can be degradable by a reactive oxygen and nitrogen species (RONS).

In embodiments of this aspect of the disclosure, the nanoparticle core can comprise a superconducting polymer.

In these embodiments of this aspect of the disclosure, the superconducting polymer can be selected from the group consisting of: Poly[2-methoxy-5-(2-ethylhexyl-oxy)-1,4-phenylene-vinylene], Poly[2-methoxy-5-(2-ethylhexyloxy)-1,4-(1-cyanovinylene-1,4-phenylene)]; Poly[(9,9-dioctyl-2,7-divinylenefluorenylene)-alt-co-(9,10-anthracene)], Poly[{9,9-dihexyl-2,7-bis(1-cyanovinylene)fluorenylene}-alt-co-{2,5-bis(N,N'-diphenylamino)-1,4-phenylene}], Poly[(9,9-dioctylfluorenyl-2,7-diyl)-alt-(benzo[2,1,3]thiadiazol-4,7-diyl)], Poly[2,7-(9,9-di-octyl-fluorene)-alt-4,7-bis(thiophen-2-yl)benzo-2,1,3-thiadiazole], Poly[2,6-(4,4'-bis(2-ethylhexyl)dithieno[3,2-b:2',3'-d]silole)-alt-4,7(2,1,3-benzothiadiazole)], Poly[2,7-(9,9-di-octyl-fluorene)-alt-4,7-bis(thiophen-2-yl)benzo-2,1,3-thiadiazole], Poly[N-9'-heptadecanyl-2,7-carbazole-alt-5,5-(4',7'-di-2-thienyl-2',1',3'-benzothiadiazole)], Poly[3-hexylthiophene-2,5-diyl], and Poly[2,5-bis(3-dodecylthiophen-2-yl)thieno[3,2-b]thiophene].

In embodiments of this aspect of the disclosure, the detectable signal emitter can be a fluorophore and the signal emitted therefrom is quenched by FRET to the quencher.

In embodiments of this aspect of the disclosure, the nanoparticle probe can be an $NH_2$-functionalized conjugated polymer nanoparticle ($NH_2$-CPN) comprising a core nanoparticle comprising: poly[9,9'-dihexyl-2,7-bis(1-cyanovinylene)fluorenylene-alt-co-2,5-bis(N,N'-diphenylamino)-1,4-phenylene] (PCFDP) and the hydrophobic lipid tails of 1,2-Dimyristoyl-sn-glycero-3-phosphoethanolamine-N-[methoxy(polyethylene glycol)-2000] (DSPE-PEG) and 1,2-distearoyl-sn-glycero-3-phosphoethanolamine-N-[amino(polyethylene glycol)-2000] (DSPE-PEG-$NH_2$), whereby the N-[methoxy(polyethylene glycol)-2000] domain of the DSPE-PEG, and the N-[amino(polyethylene glycol)-2000] domain of the DSPE-PEG-$NH_2$ comprise the shell substantially surrounding the core nanoparticle; and the dye (IR-775-COOH) conjugated to the shell.

In embodiments of this aspect of the disclosure, the detectable signal emitter of the nanoparticle probe can be a fluorophore, and wherein the step (c) can comprise irradiating the human or non-human animal subject, or a tissue thereof, with an incident radiation inducing fluorescence by the fluorophore.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLE

Example 1

Chemicals.

All chemicals were obtained from Sigma-Aldrich unless otherwise stated. [9,9'-dihexyl-2,7-bis(1-cyanovinylene) fluorenylene-alt-co-2,5-bis(N,N'-diphenylamino)-1,4-phenylene] (PCFDP) was from American Dye Source. 1,2-Dimyristoyl-sn-glycero-3-phosphoethanolamine-N-[methoxy(polyethylene glycol)-2000] (DSPE-PEG) and 1,2-distearoyl-sn-glycero-3-phosphoethanolamine-N-[amino (polyethylene glycol)-2000] (DSPE-PEG-NH$_2$) were from Avanti Lipids. 1-Ethyl-3-(3-dimethylaminopropyl)carbodiimide (EDC) was from TCI America. IR-775-COOH was synthesized according to Oushiki, D. et al., (2010) *J. Am. Chem. Soc.* 132: 2795-2801, incorporated herein by reference in its entirety.

Example 2

General Methods:

TEM images were obtained on a JEM 1230 transmission electron microscope with an accelerating voltage of 200 kV. Dynamic light scattering (DLS) experiments were performed on a 90 plus particle size analyzer (Brookhaven Instruments Corporation). The Malvern ZetaSizer Nano S was used for zeta potential measurements. UV-vis spectra were recorded on an Agilent spectrophotometer. PL measurements were carried out on a wavelength-calibrated FluoroMax-3 fluorometer (Horiba Jobin Yvon). The quantum yields were measured using fluorescein as the standard with known quantum yield of 95% in 0.1 M NaOH.

Example 3

Preparation of NH$_2$-CPN:

DSPE-PEG (1.25 mg) and DSPE-PEG-COOH (1.25 mg) were dissolved into a THF solution of PCFDP (0.25 mg/mL, 1 mL). The mixture was then rapidly poured into distilled-deionized water (9 mL) under continuous sonication with a microtip-equipped probe sonicator (Branson, W-150) at a power output of 6 watts RMS for 1 min. Then THF was evaporated at 45° C. under nitrogen atmosphere. Finally, the aqueous solution was filtered through a 0.22 μm polyvinylidene fluoride (PVDF) syringe driven filter (Millipore). The obtained nanoparticle solution was stored in dark at 8° C.

Example 4

Preparation of NanoDRONE Nanoprobes:

10×PBS (150 μL, pH=7.4) was added to NH$_2$-CPN solution (1.35 mL, 0.05 mg/mL in ultrapure water). Then, IR-775-COOH (30 μL, 1 mg/mL) and EDC (30 μL, 5 mg/mL) were added to the NH$_2$-CPN solution and the mixture was incubated at room temperature for 1.5 h. Finally, the resulting conjugates were purified by passing through a size exclusion column (NAP-10) to remove salts and unconjugated IR-775-COOH. The nanoparticle solution was further concentrated to 0.05 mg/mL (based on PCFDP) by ultrafiltration and stored in dark at 8° C. According to their absorption coefficients, the weight ratio of the dye to PCFDP is 1:5.

Example 5

Cell Culture:

HeLa cervical adenocarcinoma epithelial cells, RAW 264.7 murine macrophage cells, HL60 promyelocytic leukemia promyeloblast cells, and RWPE-1 prostate normal epithelial cells were from the American Type Culture Collection (ATCC). HeLa and RAW 264.7 cells were cultured in DMEM (Dulbecco's Modified Eagle Medium) (GIBCO) supplemented with 10% FBS (fetal bovine serum) (GIBCO). HL60 cells were cultured in Iscove's Modified Dulbecco's Medium (IMDM) (GIBCO) supplemented with 20% FBS. RWPE-1 cells were cultured in Keratinocyte Serum Free Medium (K-SFM) kit (GIBCO) supplemented with 0.05 mg/ml bovine pituitary extract (BPE) and 5 ng/ml human recombinant epidermal growth factor (EGF). All cell lines were maintained in an atmosphere of 5% CO$_2$ and 95% humidified air at 37° C.

Example 6

Cytotoxicity Test:

Cells were seeded in 96 well plates (1000 cells in 100 μL per well) for 24 h, and then NanoDRONE (final concentration 0.5, 1, 2, and 8 μg/mL) was added to the cell culture medium. Cells were incubated with or without (control) NanoDRONE for 24 h, followed by the addition of MTT (20 μL, 5 mg/mL) for 3 h. The media was removed and DMSO (200 μL) was added into each well and gently shaken for 10 min at room temperature to dissolve all formed precipitate. The absorbance of MTT at 550 nm was measured by using a microplate reader. Cell viability was expressed by the ratio of the absorbance of the cells incubated with NanoDRONE solution to that of the cells incubated with culture medium only.

Example 7

Detection of Endogenous NO of RAW 264.7:

RAW 264.7 cells were seeded into 8-well chamber slides and allowed to adhere for 18 h in a humidified atmosphere of 5% CO$_2$ and 95% air at 37° C. LPS (final 1 μg/mL) was added and incubated for 12 h. The cells were then treated with NanoDRONE (final 1.5 μg/mL) for 3 h. Alternatively, LPS (final 1 μg/mL) was added and incubated for 10 h, which was followed by addition of PTIO (1 μg/mL). After an additional incubation of 2 h, the cells were treated with NanoDRONE (final 1.5 μg/mL) for 3 h. Before the fluorescence microscopy experiments, the cells were washed three times with 1×PBS buffer and the fluorescence images were acquired through an Olympus inverted fluorescence microscope (IX2-UCB) equipped with a Nuance multispectral imaging camera. Control experiments with HeLa cells were conducted in the same manner.

Example 8

Detection of Endogenous RONS of DMSO-Differentiated HL60:

HL60 cells were first differentiated to a neutrophil-like phenotype by culturing 3×10$^5$ cells/mL in IMDM supplemented with 20% FBS and 1.3% DMSO for 7 days. Cells were concentrated, suspended in Hanks' balanced salts solution (HBSS), and added to 96 well plates at a final concentration of 1×10$^6$ cells/mL. NanoDRONE (final 0.1 μg/mL based on PCFDP) was added after incubation with PMA (1.5 μg/mL) or PMA (1.5 μg/mL)/SOD (90 mU/mL) for 3 h. The fluorescence changes of the cell suspension were monitored at $\lambda_{em}$=678 nm upon excitation at 405 nm using a TECAN Safire plate reader.

Example 9

Inflammation Models:

Female nu/nu mice (8-10 wk old) were from Charles River Laboratories International, Inc. (Mass., USA). LPS-induced peritonitis was initiated as described in Kundu et al. (2009) *Angew Chem. Int. Ed. Engl.* 48; 299-303, Lee et al., (2007) *Nat. Mater.* 6: 765-769, Yuan et al., (2012) *J. Am. Chem. Soc.* 134: 1200-1211, incorporated herein by reference in their entireties. Hyperspectral fluorescence imaging was performed on a CRi Maestro whole animal imaging system (Caliper Life Sciences, Mass., USA) using an excitation filter of 455±25 nm, a long-pass emission filter of 490 nm, and an acquisition wavelength range of 620 nm to 950 nm at 10 nm steps. Imaging occurred 4 h after the intraperitoneal injection of 1 mg LPS and immediately following intraperitoneal injection of 0.05 mg fluorescent probe or 300 mL saline injection. For the group receiving concurrent PTIO, 0.9 mmol of PTIO were injected i.p. 15 mins before LPS, and again 15 mins before NanoDRONEs. Fluorescence deconvolution and image quantitation using the peritoneal cavity as region of interest was performed using Nuance® v.3.0.1.2 software (Caliper Life Sciences, Mass., USA). Mice were euthanized by $CO_2$ asphyxiation and the skin was resected to expose the peritoneal cavity.

For the spontaneous *Corynebacterium bovis* infection model, mice were monitored for the appearance of small dorsal raised, red lesions, at the first sign of which 0.075 mg of NanoDRONEs were injected into the tail vein. Imaging was performed on the Maestro imaging system, and fluorescence deconvolution and image quantitation using the whole mouse as region of interest was performed using Nuance software.

For the mouse ear hole punch model, NanoDRONEs were injected intravenously into nude mice and pre-injury hyperspectral images were acquired on the Meastro system 4 hours later. A 2 mm hole was punched in the distal pina using a thumb-style ear punch, and images were acquired serially for 30 min. Fluorescence deconvolution and image quantitation using the ear as region of interest was performed using Nuance software.

For assessment of different stages of inflammation and restitution, ear holes were induced in the left and right ears, and the mice were left to heal for 14 d and 24 h, respectively, prior to the intravenous administration of 0.075 mg of nanoprobe.

Example 10

Biodistribution and Half-Life Measurement:

For biodistribution studies, mice received either saline or 0.1 mg of NanoDRONEs intravenously and were euthanized by $CO_2$ asphyxiation 4, 8, and 24 h after injection. Organs were resected and 100 to 200 mg of tissues were homogenized in 0.5 mL saline, and the suspensions were centrifuged. 100 mL of supernatant were added to 96 well plates, along with a standard curve of SIN-1-activated Nano-DRONEs, and the fluorescence intensity was determined on an IVIS spectrum fluorescence imager (Caliper Life Sciences, Mass., USA) following nanoprobe activation. To determine the circulation half-life of the formulation, 3 drops of blood were collected into heparin-coated tubes from the saphenous vein of animals prior to injection, and 1, 2, 4, 6, and 24 h after intravenous injection of 0.1 mg of NanoDRONES. NanoDRONEs were activated by SIN-1 and the fluorescence intensity was determined on a Fluoromax-3 spectrofluorometer (Horiba Scientific, N.J., USA).

Example 11

Histology:

Mouse skin (*C. bovis* spontaneous infection model) or mouse ears (ear hole punch tissue trauma model) were collected after euthanasia by $CO_2$ asphyxiation, fixed in buffered formalin, and embedded in paraffin. Serial 4 mm sections were mounted, half of which were stained with hematoxylin and eosin, and the other half left unstained for interrogation of NanoDRONE fluorescence in tissue using an Olympus IX8 inverted fluorescence microscope (Olympus USA, Inc., Pa., USA) fitted with a Nuance hyperspectral fluorescence camera (Caliper Life Sciences, Mass., USA). For microscopy, an excitation of 470±20 nm, a long-pass 520 nm emission filter, and an acquisition wavelength range from 620 nm to 720 nm. Image acquisition was done with Nuance v. 3.0.1.2 software.

Example 12

Statistical Analysis:

Results are expressed as the mean±standard deviation unless otherwise stated. Statistical comparisons between three groups (LPS model) were determined by one-way ANOVA and post-hoc Tukey's HSD test. Time course analysis between non-activated and activated NanoDRONE signals (spontaneous infection model and sterile injury model) was performed by general linear model repeated measures analysis. For all tests, $p<0.05$ was considered statistically significant. All statistical calculations were performed using SPSS v. 17 (IBM, N.Y., USA).

What is claimed:

1. A composition comprising a nanoparticle probe comprising a nanoparticle core comprising a detectable signal-emitting superconducting polymer, a shell attached to the superconducting polymer core by hydrophobic tails and having surface exposed reactive groups, wherein said reactive groups form covalent bonds with a quencher moiety, wherein the nanoparticle probe is an $NH_2$-functionalized conjugated polymer nanoparticle ($NH_2$-CPN) comprising a core nanoparticle comprising poly[9,9'-dihexyl-2,7-bis(1-cyanovinylene)fluorenylene-alt-co-2,5-bis(N,N'-diphenylamino)-1,4-phenylene] (PCFDP) and the hydrophobic lipid tails of 1,2-Dimyristoyl-sn-glycero-3-phosphoethanolamine-N-[methoxy(polyethylene glycol)-2000] (DSPE-PEG) and 1,2-distearoyl-sn-glycero-3-phosphoethanolamine-N-[amino(polyethylene glycol)-2000] (DSPE-PEG-$NH_2$), whereby the N-[methoxy(poly ethylene glycol)-2000] domain of the DSPE-PEG, and the N-[amino (polyethylene glycol)-2000] domain of the DSPE-PEG-$NH_2$ comprise the shell substantially surrounding the core nanoparticle; and the quencher is the dye (2-[2-[2-Chloro-3-[2-(1,3-dihydro-1,3,3-trimethyl-2H-indol-2-ylidene)-ethylidene]-1-cyclohexen-1-yl]-ethenyl]-1,3,3-trimethyl-3H-indolium chloride conjugated to the shell.

2. The composition of claim 1, further comprising a pharmaceutically acceptable carrier.

3. A nanoparticle probe comprising:
    (i) a nanoparticle core consisting of the detectable signal-emitting superconducting polymer poly[9,9'-dihexyl-2, 7-bis(1-cyanovinylene)fluorenylene-alt-co-2,5-bis(N, N'-diphenylamino)-1,4-phenylene] (PCFDP) and the hydrophobic lipid tails of 1,2-dimyristoyl-sn-glycero- 3-phosphoethanolamine-N-[methoxy(polyethylene glycol)-2000] (DSPE-PEG) and 1,2-distearoyl-sn-glycero-3-phosphoethanolamine-N-[amino(polyethylene glycol)-2000] (DSPE-PEG-NH$_2$);

(ii) a shell substantially surrounding the said nanoparticle core, said shell consisting of the N-[methoxy(polyethylene glycol)-2000] domains of the DSPE-PEG and the DSPE-PEG-NH$_2$ of the core, wherein said N-[methoxy(polyethylene glycol)-2000] domains have reactive groups forming covalent bonds with a quencher moiety; and (iii) a quencher moiety, wherein said quencher moiety is the dye (2-[2-[2-Chloro-3-[2-(1,3-dihydro-1,3,3-trimethyl-2H-indol-2-ylidene)-ethylidene]-1-cyclohexen-1-yl]-ethenyl]-1,3,3-trimethyl-3H-indolium chloride degradable by a reactive oxygen and nitrogen species (RONS).

4. A method of detecting a site of generation of a reactive oxygen or nitrogen species (RONS) in a human or non-human animal subject comprising the steps of:

(a) administering to a human or non-human subject a pharmaceutically acceptable composition of the nanoparticle probes of claim 1:

(b) allowing the nanoparticle probes of the administered pharmaceutically acceptable composition to contact a site of inflammation in the subject animal or human;

(c) generating a detectable signal from the detectable signal emitting polymer;

(d) detecting the signal emitted from the detectable signal emitting polymer; and (e) locating the position of the detectable signal relative to the anatomy of the human or non-human animal subject, thereby identifying a site of generation of a reactive oxygen or nitrogen species (RONS) in the human or non-human animal subject.

5. The method of claim 4, wherein the site of generation of a reactive oxygen or nitrogen species (RONS) is an inflammation of a tissue of the human or non-human animal or an injured tissue.

6. The method of claim 4, wherein the pharmaceutically acceptable composition is administered to the human or non-human animal subject topically, intravenously, intraperitoneally, or by injection to a site suspected of being inflamed.

7. The method of claim 4, wherein the quencher is linked to the detectable signal emitting polymer by a linker cleavable by a reactive oxygen and nitrogen species (RONS).

8. The method of claim 4, wherein the quencher is degradable by a reactive oxygen and nitrogen species (RONS).

9. The method of claim 4, wherein the detectable signal emitting polymer is a fluorophore and the signal emitted therefrom is quenched by FRET to the quencher.

10. The method of claim 4, wherein the detectable signal emitting polymer of the nanoparticle probe is a fluorophore, and wherein the step (c) comprises irradiating the human or non-human animal subject, or a tissue thereof, with an incident radiation inducing fluorescence by the fluorophore.

* * * * *